United States Patent
Ziv

(10) Patent No.: US 9,333,329 B2
(45) Date of Patent: May 10, 2016

(54) VAGINAL CARRIER FOR THE CONTROLLED RELEASE OF SUBSTANCES

(76) Inventor: Elan Ziv, Ramat-Gan (IL)

(*) Notice: Subject to any disclaimer, the term of this patent is extended or adjusted under 35 U.S.C. 154(b) by 579 days.

(21) Appl. No.: 12/921,158

(22) PCT Filed: Mar. 2, 2009

(86) PCT No.: PCT/IL2009/000240
§ 371 (c)(1),
(2), (4) Date: Sep. 6, 2010

(87) PCT Pub. No.: WO2009/109966
PCT Pub. Date: Sep. 11, 2009

(65) Prior Publication Data
US 2011/0034901 A1    Feb. 10, 2011

Related U.S. Application Data

(60) Provisional application No. 61/064,394, filed on Mar. 4, 2008.

(51) Int. Cl.
*A61M 31/00* (2006.01)
*A61M 37/00* (2006.01)
*A61K 9/02* (2006.01)
*A61K 9/00* (2006.01)

(52) U.S. Cl.
CPC .......... *A61M 31/002* (2013.01); *A61K 9/0036* (2013.01); *A61K 9/02* (2013.01); *A61M 31/007* (2013.01); *A61M 37/0069* (2013.01)

(58) Field of Classification Search
CPC ............ A61M 31/007; A61M 31/002; A61M 37/0069; A61K 9/02; A61K 9/0036
USPC ........... 604/515, 191, 330, 332, 271, 385.17, 604/385.18, 275, 257, 258, 514, 279
See application file for complete search history.

(56) References Cited

U.S. PATENT DOCUMENTS

| 2,902,821 | A | * | 9/1959 | Kelly, Jr. | 59/80 |
| 4,012,496 | A | | 3/1977 | Schöpflin et al. | |
| 4,244,542 | A | * | 1/1981 | Mathews | 248/49 |
| 4,246,896 | A | | 1/1981 | Horne, Jr. et al. | |
| 6,641,518 | B2 | * | 11/2003 | Wolfson et al. | 600/6 |
| 6,733,485 | B1 | * | 5/2004 | Whitehurst et al. | 604/500 |
| 6,899,700 | B2 | * | 5/2005 | Gehling et al. | 604/285 |

(Continued)

FOREIGN PATENT DOCUMENTS

| GB | 1430533 | 3/1976 |
| WO | WO 99/22680 | 5/1999 |
| WO | WO 2009/109966 | 9/2009 |

OTHER PUBLICATIONS

Alexander et al., Why consider vagina drug administration, Jul. 2004, Fertility and Sterility, vol. 82, No. 1, p. 1-12.*
International Search Report Dated Jul. 16, 2009 From the International Searching Authority Re.: Application No. PCT/IL2009/000240.

(Continued)

*Primary Examiner* — Bhisma Mehta
*Assistant Examiner* — Lauren M Peng

(57) ABSTRACT

A device that delivers one or more substances into a vaginal lumen according to one of a plurality of release patterns. The device comprises a supporting structure, substance dispensers, and/or coupling elements which are configured to release one or more substances, for example, drugs, in manner designed to optimize treatment of one or more medical conditions.

41 Claims, 18 Drawing Sheets

(56) References Cited

U.S. PATENT DOCUMENTS

| | | | |
|---|---|---|---|
| 6,939,336 B2* | 9/2005 | Silfver | 604/515 |
| 2002/0099359 A1 | 7/2002 | Santini, Jr. et al. | |
| 2003/0060785 A1 | 3/2003 | Lavean et al. | |
| 2004/0082937 A1 | 4/2004 | Ausiello et al. | |
| 2007/0043327 A1* | 2/2007 | Knox | A61K 9/0031 604/286 |

OTHER PUBLICATIONS

Written Opinion Dated Jul. 16, 2009 From the International Searching Authority Re.: Application No. PCT/IL2009/000240.

International Preliminary Report on Patentability Dated Sep. 16, 2010 From the International Bureau of WIPO Re. Application No. PCT/IL2009/000240.

* cited by examiner

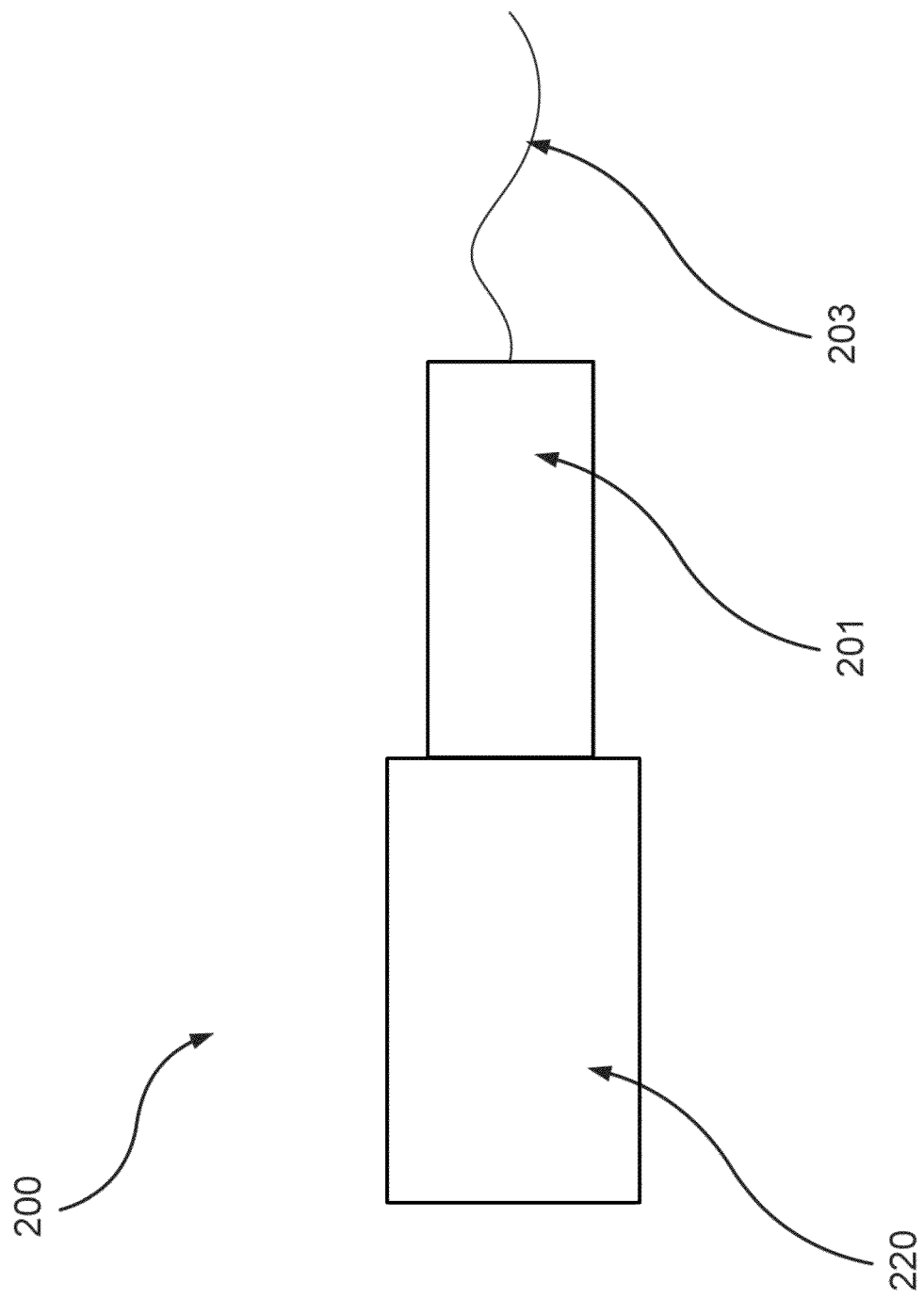

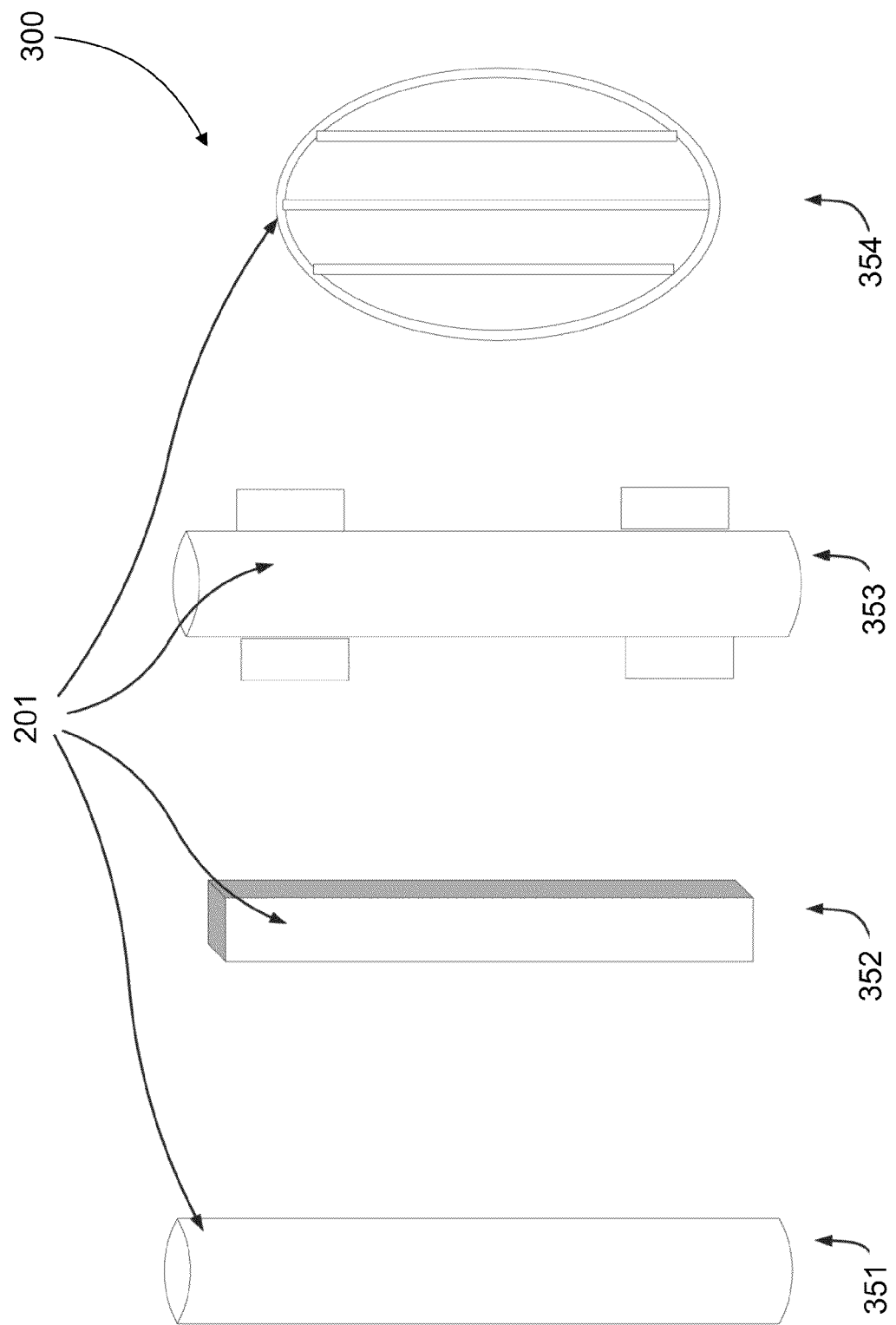

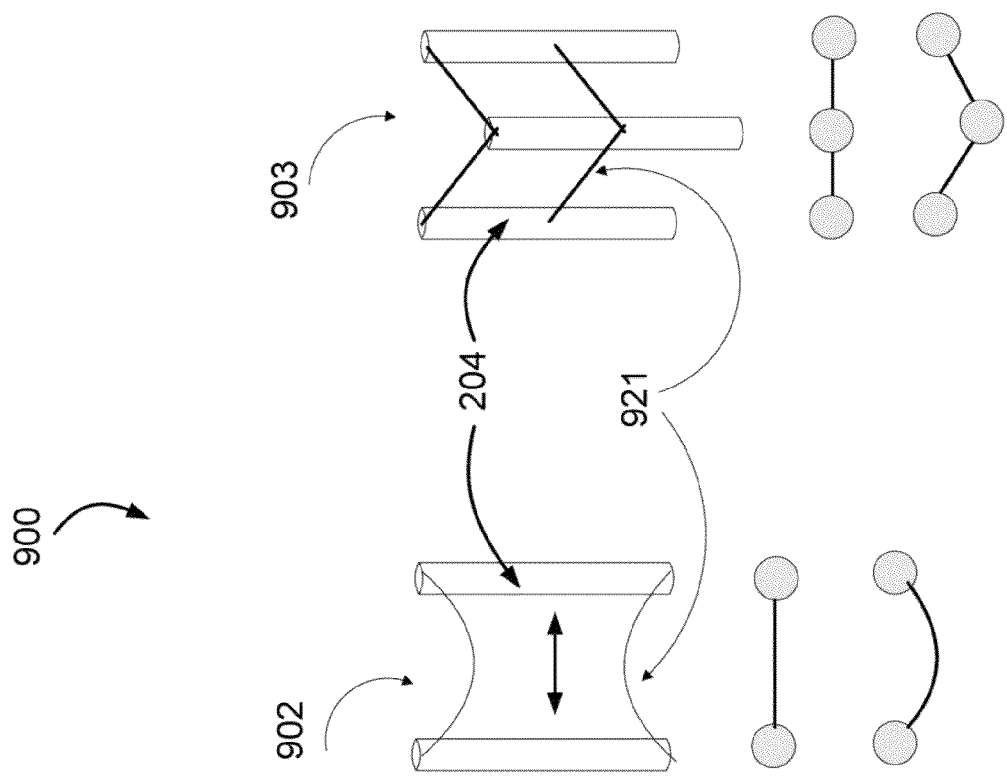
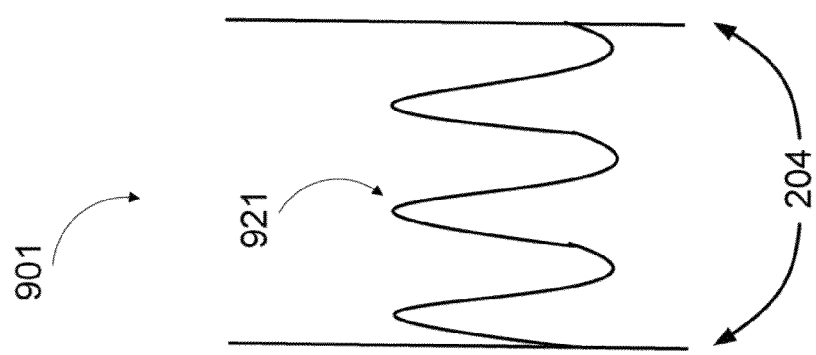
FIG. 9

VAGINAL CARRIER FOR THE CONTROLLED RELEASE OF SUBSTANCES

RELATED APPLICATIONS

This Application is a National Phase of PCT Patent Application No. PCT/IL2009/000240 having International filing date of Mar. 2, 2009, which claims the benefit of U.S. Provisional Patent Application No. 61/064,394 filed on Mar. 4, 2008. The contents of the above Applications are all incorporated herein by reference.

FIELD AND BACKGROUND OF THE INVENTION

The present invention, in some embodiments thereof, relates to medical devices and, more particularly, but not exclusively, to controlled delivery of therapeutic agents, in humans and in animal species.

Presently, most medications are consumed via several routes, mainly orally. Oral ingestion of most drugs is followed by inactivation of a large portion of those drugs while passing through the liver, and the rest of the drugs enter the blood stream in a surge, with diminishing activity over time as a result of excretion and metabolism. To maintain a constant drug level within the blood, there is a need for repeated oral ingestions.

Presently, there are 3 main non-invasive routes for drug administration: oral ingestion (e.g., tablets, fluids, powder), cutaneous absorption (e.g., patches, creams), and trans-mucosal diffusion, for example, via lungs (inhalation), via rectum (suppositories), via vagina (e.g., tablets, creams, pessaries), and other locations (e.g., ears, nose, eyes).

Though oral ingestion of drugs is the most prevalent method for drug administration, there are several reasons why some drugs need a different route:
- to bring the lowest needed dose of the active molecule as close as possible to the target organ with minimal or no influence on other parts of the body;
- to refrain from some adverse events related to the alimentary tract (e.g. ingestion of aspirin and its derivatives that may adversely affect the stomach);
- to avoid the loss of some of the drug while passing from the bowl to the blood stream (hepatic first pass metabolism);
- to prevent drug related complaints which are usually due to the immediate elevation (surge) of drug's plasma levels;
- to obtain a continuously low level of drug within the plasma, acting continuously on a target organ, without peaks which may allow for the use of very low amounts of drug which is not always possible with oral administration;
- ongoing reluctance of many people to ingestion of many drugs, in the face of the growing need for administration of several medications at the same time; inability of some people to swallow oral medications.

As mentioned above, mucosal routes for drug administration are promising, among them the vaginal route. The vagina has unique features for drug absorption which can be exploited in order to achieve desirable therapeutic effects. The vagina is a hollow organ with 3 planes. Its dimensions (length and diameter) vary between different women. Most of a vaginal surface is covered with stratified squamous epithelium without glands, nonetheless, it secretes large amounts of fluid. Some of the fluid comes from cervical secretions, and some is a transudate from the very rich vascular plexus around it. The uppermost part of the vagina contains goblet cells which secrete mucous; hence this part acts as a mucous membrane, being able to absorb medications in a somewhat different manner. These secretions play a large role in the absorption mechanism as they allow some of a drug to mix with the fluid (hence larger absorption surface) and it also maintains the proper pH for better absorption.

An important feature of the vagina is the huge vascular plexus surrounding it. The venous drainage of the vagina, mainly of its uppermost part, is very tortuous and empties into two different venous systems, thus drugs absorbed from the vaginal epithelium may escape first-pass hepatic metabolism. Due to the abundance of blood vessels, mainly at the upper part of the vagina, there is a transport of chemicals from draining veins into the arteries that lead into the uterus. This gives rise to the existence of "first uterine pass" theory, suggesting that medications absorbed from the deep part of the vagina will act on the uterus first, prior to any action anywhere else in the body.

The administration of a drug substance may be effected to induce either a local or systemic effect. Local therapies are usually aimed at treating infections of various kinds, and vaginal atrophy. Vaginal administration for systemic therapies takes advantage of the highly vascularized vaginal tissue without hepatic first pass metabolism, hence the need for much lower doses in order to achieve therapeutic serum concentration. The systemic absorption of the drug requires a number of well known steps—release from the delivery system, drug dissolution in vaginal fluid, and absorption across vaginal epithelium.

The vagina is surrounded by various organs, which may be treated vaginally as well as by oral ingestion. The bladder and the urethra are situated anterior to the vagina. The uterus and its cervix are located at the top of the vagina, and the rectosigmoid is next to the posterior wall of the vagina.

Current medical treatments performed through the vagina may belong to one or more of the following 3 categories:
1. Local reactants—function on vaginal wall only, with minimal, if any, absorption beyond vaginal walls. Such medications are usually intended to treat infections, vaginal atrophy, or serve as a spermicide. These medications may belong to one of the following two groups: conventional drug delivery systems, marketed as creams and gels, vaginal tablets, pessaries and foams; and modified release formulations which may be distributed as films and gels.
2. Systemic reactants—destined to be absorbed systemically and affect distant organs. These medications, which are regarded as "modified release formulations" may appear as films and rings.
3. Surrounding organ reactants—destined to be absorbed beyond vaginal wall and affect neighboring organs, such as the uterus or the urinary bladder. These medications also belong to the "modified release formulation" and appear as films or rings.

Local reactants are destined to function on vaginal wall or in close proximity. Most of the known drug delivery systems to the vagina have severe drawbacks such as leakage of the drug (as with creams, gels, and melted pessaries), limited residence time of the formulation on the vaginal wall due to gravity, motion, and poor adherence capacity of the drug or its carrier, the presence of menstrual cycle, local irritation by some of the drug carriers (tablets or pessaries), and personal care habits. In some cases, the vaginal normal flora, mainly the *Lactobacillus Acidophilus*, may be damaged, giving rise to abnormal flora. Some of these medications are designed be inserted manually by the user, a procedure not always welcome by all women. The affect of the drug is usually during a short period, and there is no way to stop it once applied into the vagina. Also, only a relatively small number of medications may be utilized by this route, without the ability to target a specific vaginal wall or adjacent organ.

Reactants destined to be absorbed systemically or function on adjacent organs such as the uterus or the bladder, are usually attached to a specific carrier that provides unique capabilities according to needs, such as the ability to supply the reactants in high doses, constant availability and constant touch with the vaginal mucosa.

Reference is now made to FIG. 1 which is a schematic illustration that pictorially shows a carrier used for controlled release of drugs via the vaginal mucosa. This carrier is a flexible ring, made of flexible polymers such as silicones, ethylene vinyl acetate (EVA), or styrene butandiene block copolymer. These rings are designed to release drugs in a controlled fashion after insertion into the vagina. Advantages of such a drug carrier are that it is user controlled, it is not messy, and it releases the drug constantly, hence there is no need for daily ingestion of medication. In most cases, ring carriers have a diameter of 50-55 millimeters and a cross sectional width of 4-9 millimeters. Drugs are contained within the ring either homogeneously dispersed within the polymer, or as a reservoir or a sandwich from which the drugs are absorbed into the mucosa.

After insertion into the vagina, the drug is released from the polymer into the vaginal fluid, from which it is further absorbed by various mechanisms into the sub-mucosal layers, and deeper into the blood stream.

The ring has several disadvantages as a carrier for drug release. Among them is the need to insert it manually, having to insert fingers into the vagina, and remove it in the same manner, with a finger. As a ring, it is impossible to direct the drug towards a specific organ, such as the bladder or uterus, hence the inability to affect a specific pelvic organ. Also, as a solid ring it is difficult to supply various drugs on the same carrier. This problem of variable drug administration in a ring has a proposed solution in U.S. Pat. No. 6,436,428 (Mahashabde, et. al.) which describes a way to place a drug within a ring by drilling several bores along the ring in order to contain a second drug. This complicated method may allow for more than one drug to be incorporated into a ring controlled release drug carrier.

SUMMARY OF THE INVENTION

According to of some embodiments of the present invention there is provided a device for delivery of at least one medical substance in a vaginal lumen, including a configurable releasing mechanism configured for containing at least one medical substance and having a plurality of delivery configurations to actualize a plurality of predefined release patterns of the at least one medical substance, and a supporting structure for supporting the positioning of the configurable releasing mechanism in the vaginal lumen.

Optionally, the configurable releasing mechanism includes at least one of a plurality of substance dispensers, each configured according to a pattern selected from the plurality of predefined release patterns, the supporting structure and the at least one of a plurality of substance dispensers being detachably coupled to one another.

Optionally, the configurable releasing mechanism is modular.

Optionally, the device further includes at least one substance dispenser that is coupled to at least one of a plurality of predefined sites on the supporting structure.

Optionally, the device further includes at least one of the substance dispensers which is configured to be coupled at a site on the supporting structure to effect placement at an optimal anatomical location to affect an organ, and at least one other of the substance dispensers which is configured to be coupled at a site on the supporting structure at a different optimal anatomical location to affect a different organ.

Optionally, the at least one of the substance dispensers and the at least one other of the substance dispensers deliver substances simultaneously.

Optionally, the releasing mechanism self-adjusts its dimensions to conform to the spatial constraints of the vaginal lumen.

Optionally, the coupling enables situating the supporting structure and the at least one substance dispenser adjacent to the periphery of the vaginal lumen without occupying the center of the vaginal lumen to enable unhindered coitus.

Optionally, the supporting structure is configured for releasing a substance.

Optionally, the supporting structure includes a reservoir of the at least one substance and is configured for dispensing the at least one substance via the substance dispensers.

Optionally, the at least one substance dispenser is attached to the supporting structure by a means selected from the group consisting of including a fastener, a screw, a snap, a glue, a tucker, and a resin.

Optionally, a first group of the plurality of substance dispensers releases a first group of substances and a second group of the plurality of substance dispensers releases a second group of substances.

Optionally, the at least one substance dispenser has a form that is at least one of a shape and an assembly of shapes, wherein the shapes are selected from a group consisting of a cylinder, a torus, an ellipsoid, a sphere, a polyhedron, a crescent, a truncated cylinder, a truncated torus, a truncated ellipsoid, a truncated sphere, a truncated polyhedron, a truncated crescent, and an irregular solid.

Optionally, the surface of the form is selected from a group consisting of smooth, coarse, perforated, striated, dimpled, particulate, permeable, and semi-permeable.

Optionally, at least one of the at least one substance dispenser and the supporting structure is at least one of absorbable and degradable by substances present within the vaginal lumen.

Optionally, the at least one medical substance is selected from the group consisting of a drug, a chemical, a therapeutic material, a diagnostic material, a nutrient, a metabolic substance, a scent-emitting agent.

Optionally, the device further includes a sensor configured for detecting a concentration of a substance selected from the group consisting of a metabolic substance, a pathogenic substance, a biological substance, a chemical substance, and the at least one medical substance.

Optionally, the device further includes a controller configured to control a rate of release of the at least one medical substance according to the detecting.

Optionally, the rate of release is selected from the group consisting of an absence of release, a constant rate of release, and a variable rate of release.

According to of some embodiments of the present invention there is provided a kit including at least one of the following items: a container for containing at least one medical substance, a substance dispenser, a supporting structure, a medical substance, a member of a group consisting of a fastener, a screw, a snap, a glue, a resin, and a tucker, a sensor for detecting a concentration of a substance, a controller configured to control a rate of release, an applicator, and a removal device.

According to of some embodiments of the present invention there is provided a device for delivery of at least one of a plurality of disparate medical substances into a body via vaginal tissues, including a sensor configured for detecting a concentration of a substance in a vaginal lumen, a reservoir configured for containing at least one medical substance, and a controller configured to control a release of the at least one medical substance into the vaginal lumen in response to the detecting.

Optionally, the substance is selected from a group consisting of a metabolic substance, a pathogenic substance, a biological substance, a chemical substance and the at least one disparate medical substance.

According to of some embodiments of the present invention there is provided a method for delivery of at least one of a plurality of disparate medical substances into a body via a vaginal lumen, the device including assembling a device including a supporting structure and a plurality of interchangeable substance dispensers, and inserting the device into the vagina, and releasing the at least one disparate medical substance wherein the inserting includes optimizing effectiveness of the at least one disparate medical substance by orienting the device at an angle selected from the group consisting of a coronal angle, a transverse angle, and a sagittal angle.

According to of some embodiments of the present invention there is provided a method for delivery of at least one of a plurality of disparate medical substances into a body via a vagina, the device including placing a substance dispenser for dispensing first and second medical substances in a vaginal lumen, delivering the first medical substance to a first vaginal area in the vaginal lumen to affect a first organ, and simultaneously delivering the second medical substance to a second vaginal area in the vaginal lumen to affect a second organ.

Optionally, the delivery includes measuring a level of at least one a group including a metabolic substance, a pathogenic substance, a biological substance, a pathogen, a chemical substance, and the at least one of a plurality of disparate medical substances, and controlling a rate of release of the at least one of a plurality of disparate medical substances according to the measuring.

According to of some embodiments of the present invention there is provided a kit for delivery of at least one of a plurality of disparate medical substances into a body via a vagina, the kit including a plurality of substance dispensers each configured for releasing at least one substance in at least one of a plurality of predefined release patterns in the vagina, and a supporting structure configured for detachably coupling at least one of the plurality of substance dispensers.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A is a schematic drawing of a delivery device, according to some embodiments of the present invention;

FIG. 3 is a schematic drawing depicting exemplary supporting structures according to some embodiments of the present invention;

FIG. 9 is a schematic illustration depicting adjustable (expandable) delivery devices between lateral vaginal walls, according to some embodiments of the present invention.

DESCRIPTION OF EMBODIMENTS OF THE INVENTION

Figure 1:
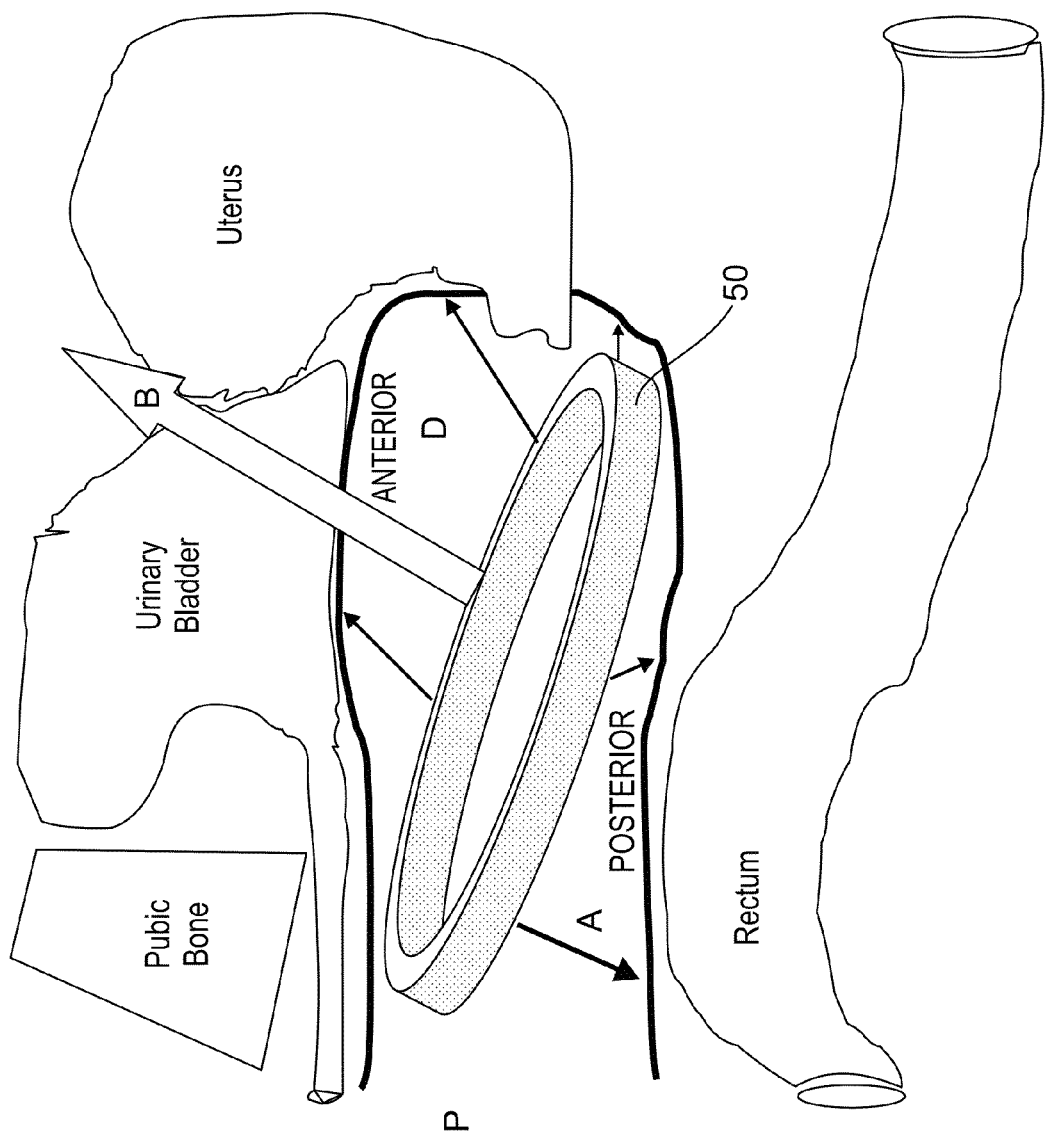
FIG. 1 is a is a schematic illustration that pictorially shows a carrier used for controlled release of drugs via the vaginal mucosa.

The present invention, in some embodiments thereof, relates to medical devices and, more particularly, but not exclusively, to controlled delivery of therapeutic agents in humans and animals.

According to some embodiments of the present invention, a device for delivery of medical substances into the body via vaginal mucosa is provided. The device is configurable to deliver one or more substances in one or more of a plurality of spatial and/or temporal release patterns. Spatial release patterns are implemented by a releasing mechanism that releases one or more substances in specific locations in a vaginal lumen. The releasing mechanism determines the size of the surface area of the vaginal walls to which the substances are released. The releasing mechanism may be designed to release the substances in various fixed and/or variable rates, which are referred to herein as temporal release patterns.

As used herein, release pattern means one or more areas of one or more vaginal walls to which one or more substances are delivered and/or one or more release rates of the one or more substances over a period at the one or more areas of the one or more vaginal walls.

As used herein, a medical substance means a substance that is used for medical therapy, treatment, nutrition, diagnostics, and/or procedures. As used herein, a supporting structure means an element of a device to which other elements of the device may be attached, and by which those other elements may be positioned. As used herein, a substance dispenser means a modular element configured to store and/or dispense a substance, and which may be attached to and/or detached from a supporting structure.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 2A is a schematic drawing of a delivery device 200, according to some embodiments of the present invention. In an embodiment of the present invention, a delivery device 200 comprises a supporting structure 201 and a releasing mechanism 220 for releasing the substance into a vaginal lumen. Optionally, the releasing mechanism 220 comprises a container for containing a substance to be released (not shown). Releasing mechanism 220 is configured to achieve a desired release pattern. Releasing mechanism 220 comprises elements and attributes that affect the release pattern. For example, delivery device 200 may be configured to implement a temporal release pattern for immediate release of a substance, delayed release of a substance, and/or controlled release of a substance. Additionally or alternatively, delivery device 200 may be configured to implement a spatial release pattern designed to exploit a particular anatomic characteristic, for example, vaginal mucosa and/or a vascular plexus. Additionally or alternatively, delivery device 200 may be configured to optimize delivery of a substance to a particular organ, for example, the uterus or the urethra, and/or delivery device 200 may be configured to optimize delivery of a systemic agent, for example, a drug to treat high levels of cholesterol.

As used herein, releasing mechanism means an aggregate of device components that determine a configured release pattern.

Optionally, delivery device 200 is configured to optimize substance delivery to a single organ and/or anatomical location. Alternatively, delivery device 200 may be configured to optimize substance delivery to multiple organs and/or anatomical areas simultaneously. Optionally, the substance being delivered by the delivery device may be a single substance; alternatively, the delivery device may deliver a plurality of substances.

The releasing mechanism may have a variety of configurable characteristics including but not limited to a configurable shape, size, surface property, and used components. The releasing mechanism implements active and/or passive release techniques, such as a diffusion, a pump, and mechanically applied pressure to eject the one or more stored substances. It should be noted that a delivery device comprising a larger substance dispenser surface area typically releases a substance at a higher rate over time than a similar delivery device comprising a smaller substance dispenser surface area. A delivery device containing a larger quantity of a substance may be configured to release a substance for a longer period of time than a similar device containing a smaller quantity of the substance. Additionally or alternatively, a delivery device containing a larger quantity of a substance may be configured to release a substance at a higher rate than a similar device containing a smaller quantity of the substance.

Optionally, a user configures delivery device 200 by assembling a plurality of modular components to supporting structure 201, including but not limited to substance dispensers, coupling elements, and/or containers for containing substances to be released.

Figure 2B:
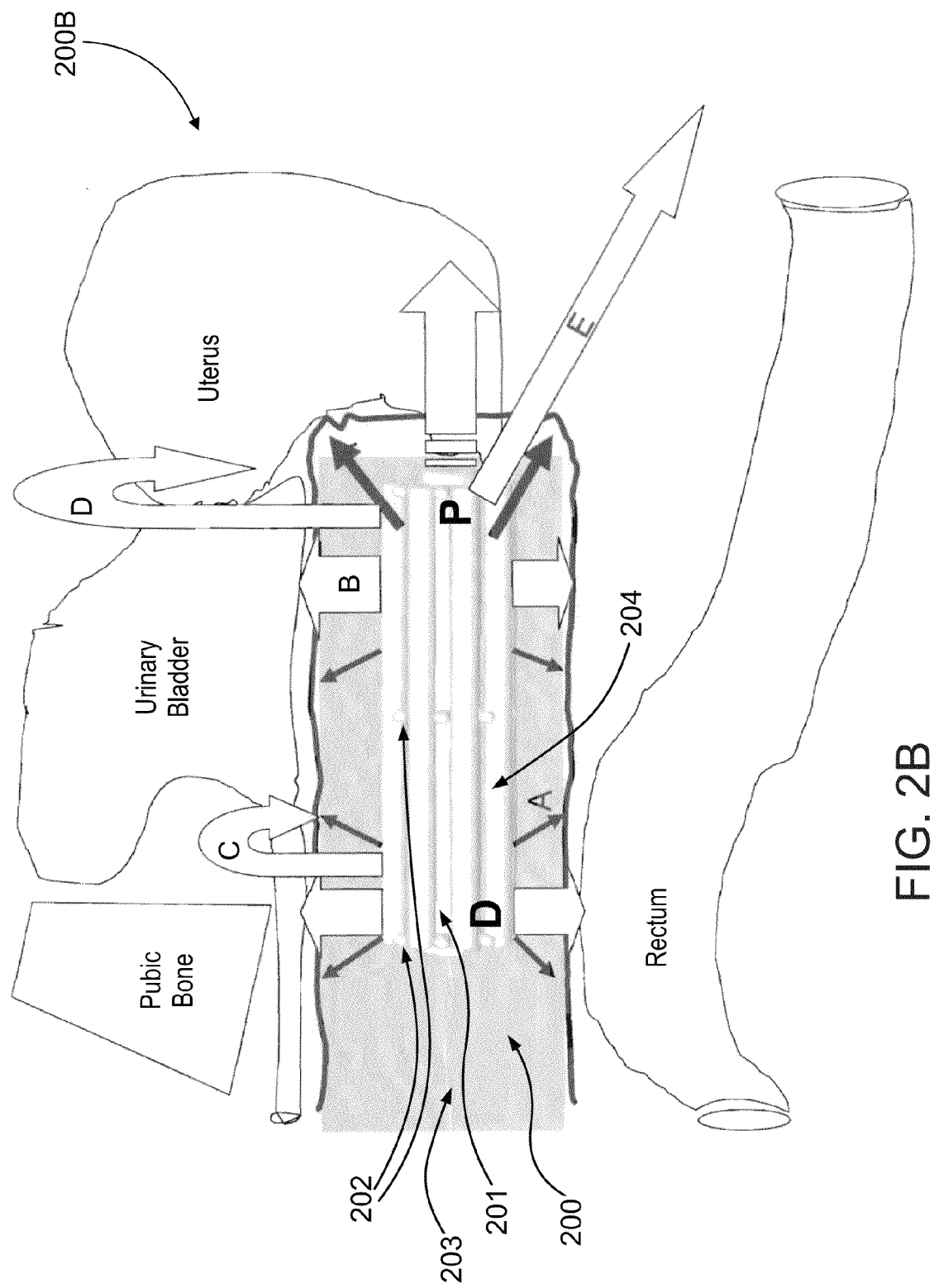
FIG. 2B is a schematic drawing of an exemplary embodiment of the invention, allowing for large contact area of one or more drugs with large surface area of the vagina.
Figure 2C:
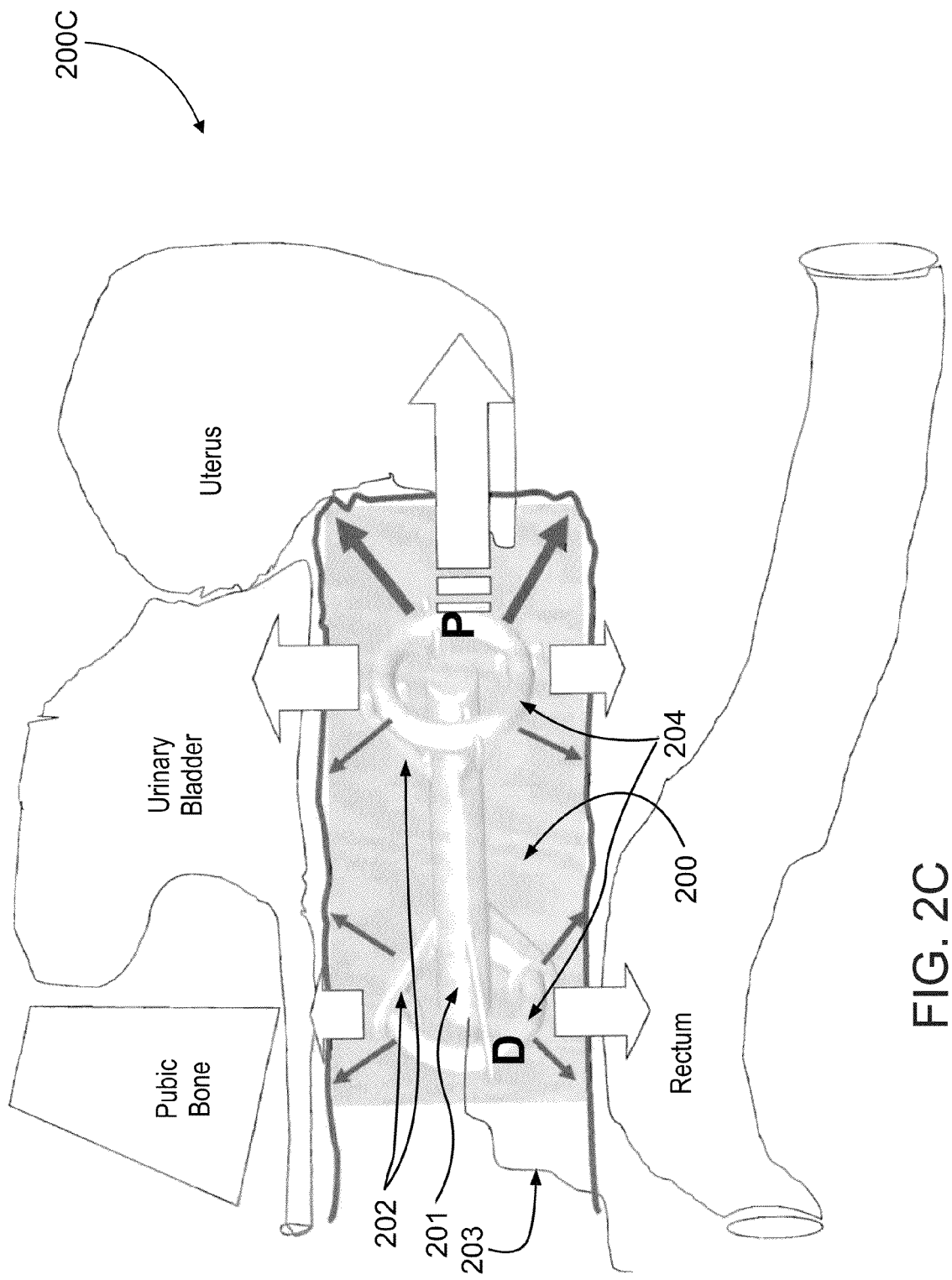
FIG. 2C is a schematic drawing of an exemplary embodiment of the invention, allowing for specific contact area of a drug with proximity to specific organs.

Reference is now also made to FIG. 2B which is a schematic drawing of a delivery device 200 wherein substance dispensers present a large surface area for releasing one or more drugs to a correspondingly large surface area of the vaginal walls, according to some embodiments of the present invention. FIG. 2C is a schematic drawing of the invention, providing for substance dispensers to release one or more drugs in proximity to specific organs, according to some embodiments of the present invention. According to an exemplary embodiment of the present invention, delivery device 200 contains one or more substances, such as medical substances, and is configurable to release them in one of a plurality of predefined spatial and/or temporal patterns within a vaginal lumen. A temporal release pattern may be set by timing of substance release rates from one or more of substance dispensers 204. Delivery device 200 may comprise modular components including supporting structure 201 and one or more substance dispensers 204 configured for delivering one or more substances, especially medical substances, into a vaginal lumen. The substance delivered into the vaginal lumen is stored in one or more containers which may be comprised in substance dispensers 204 and/or supporting structure 201. Supporting structure 201 and/or substance dispensers 204 are configured to be detachably coupled so that one of a plurality of release patterns may be implemented at a given point in time. The number of substance dispensers 204 attached to supporting structure 201 may be configured according to therapeutic and/or diagnostic requirements. Optionally, one or more coupling elements 202 may couple supporting structure 201 and substance dispensers 204 to each other. Optionally, delivery device 200 may be inserted into the vaginal lumen by means of an applicator (not shown), for example, an applicator resembling one that may be used for the insertion of a menstrual tampon. Optionally, removal of delivery device 200 from the vagina may be done by pulling a removal device, which may be a string 203, as with the menstrual tampon, or a ring (not shown) attached to the most distal part of supporting structure 201, close to the vaginal entrance. Additionally or alternatively, the delivery device 200 may be inserted and/or removed manually.

As used herein, detachably coupled means attachment of two elements to each other in a manner that enables the elements to be subsequently detached without damaging and/or negatively impacting the functionality of the elements.

Reference is now also made to FIG. 3, which is a schematic drawing depicting non-limiting exemplary embodiments of supporting structures 201 according to some embodiments of the present invention. In an exemplary embodiment of the present invention, a supporting structure 201 is formed in one of a plurality of shapes and/or sizes. Different shapes and sizes affect the resulting release pattern attributes, for example, surface area, proximity to various organs, and rate of substance release. Examples of supporting structure shapes include but are not limited to a cylinder 351, an elongated cube 352, a combination of a cylinder and elongated cubes 353, and a ring with or without elements spanning the opening in the ring 354, a tortuous snake, a dollar sign ($), an elongated infinity sign (∞), a ball, an almond, and an egg. Longitudinal supporting elements may be used when a treatment is desired for the full length of the vagina. Treatment may be for local conditions, e.g. for yeast infections, or systemic conditions, utilizing a large surface area. A structure with extensions, for example cylinder with elongated cubes 353, may be used for delivering drugs to organs at specific walls, such as the urethra and/or bladder within the anterior wall. Other springy shapes such as rings, dollar sign ($), and snakes are designed to allow intercourse, i.e., not to block the vagina. These last three configurations are springy, and are designed to anchor themselves within the vagina. In longitudinal embodiments, i.e., embodiments wherein delivery device 200 length is significantly longer than delivery device 200 width and/or diameter, supporting structure 201 has two poles: a proximal pole (P) that is closer to the uterine cervix and a distal pole (D) that faces the entrance to the vagina; supporting structure 201 may be of various lengths, for example between 1 and 7 centimeters. A cross-section of a longitudinal supporting structure 201 may be round, square, polygonal, elliptical, and/or irregular in accordance with the desired release pattern and/or therapeutic considerations. A substance dispenser 204 may be directly and/or indirectly attached to supporting structure 201 by means of a fastener, a screw, a snap, glue, a resin. Optionally or alternatively, substance dispensers 204 may be indirectly attached to supporting structure 201 by means of one or more coupling elements (described below).

Figure 4A:
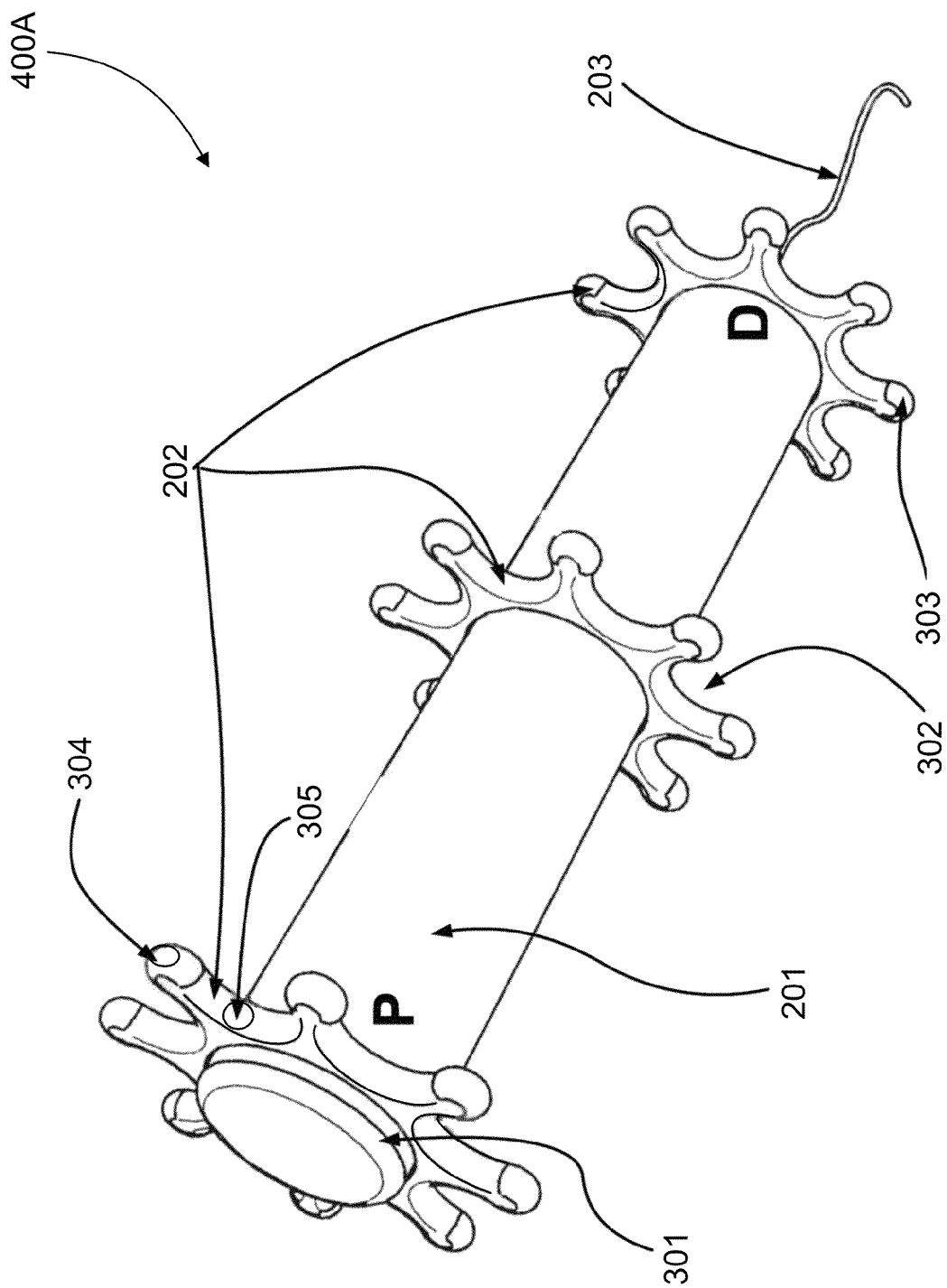
FIG. 4A is a schematic drawing depicting an exemplary supporting structure and exemplary coupling elements according to some embodiments of the present invention.
Figure 4B:
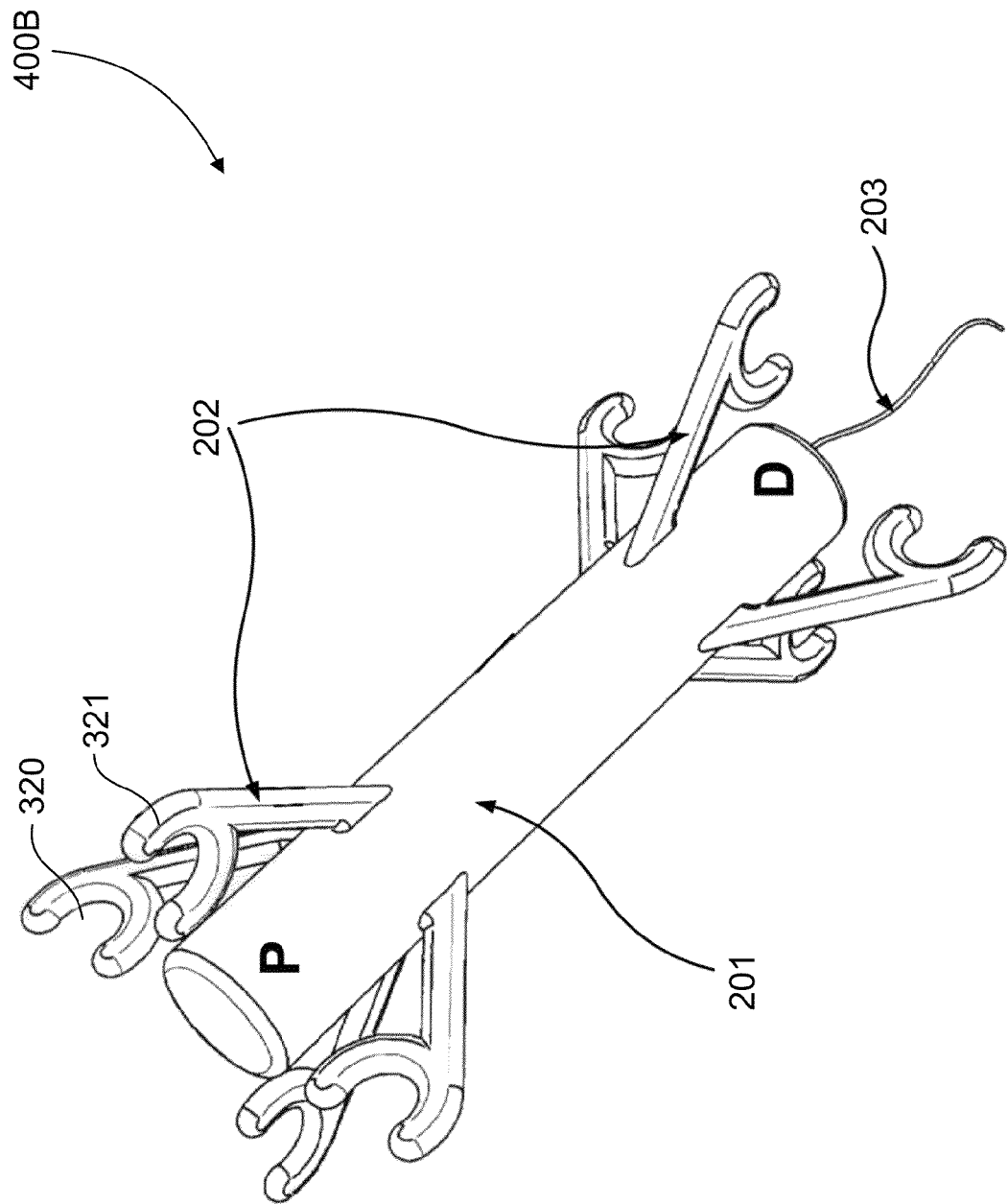
FIG. 4B is a schematic drawing depicting an exemplary supporting structure and exemplary coupling elements according to some embodiments of the present invention.

Reference is now also made to FIG. 4A and FIG. 4B which are schematic drawings depicting exemplary embodiments of supporting structures 201 with coupling elements 202, according to some embodiments of the present invention. FIG. 4A depicts an exemplary supporting structure 201 with coupling elements 202 to which one or more substance dispensers 204 may be attached, for example, longitudinally, substantially parallel to the supporting structure 201. An exemplary coupling element 202 as illustrated in FIG. 4A comprises a body with a central hole 301, the hole having the structure of a cut section of supporting structure 201 to which it is attached. Such coupling elements 202 may slide along supporting structure 201, and the number of coupling elements 202 may vary as needed, for example 2 to 4. These coupling elements 202 have recesses 302 for insertion of substance dispensers 204 between rounded spikes 303. The number of recesses may be determined by the need for a particular drug administration and/or release pattern, for example, a need for a particular distribution of drug around vaginal walls. Examples of numbers of recesses that may be comprised in a coupling element 202 include 2, 4, 8, and 16. FIG. 4B depicts an exemplary supporting structure 201 with coupling elements 202 to which one or more substance dispensers 204 may be attached, for example, at proximal (P) and/or distal (D) ends of supporting structure 201. The proximal (P) end of supporting structure 201 is close to the uterus, and a distal (D) pole, close to the vaginal introitus, to which a removal device, for example, a string 203 or a ring (not shown), may be attached.

In some embodiments of the present invention, supporting structure 201 may comprise a reservoir of one or more substances which are supplied to substance dispensers 204 through a coupling element 202, for example as illustrated in FIG. 4A, through nozzles 304 located at the tip of coupling element 202 or through tunnels 305 in coupling element 202.

Figure 5A:
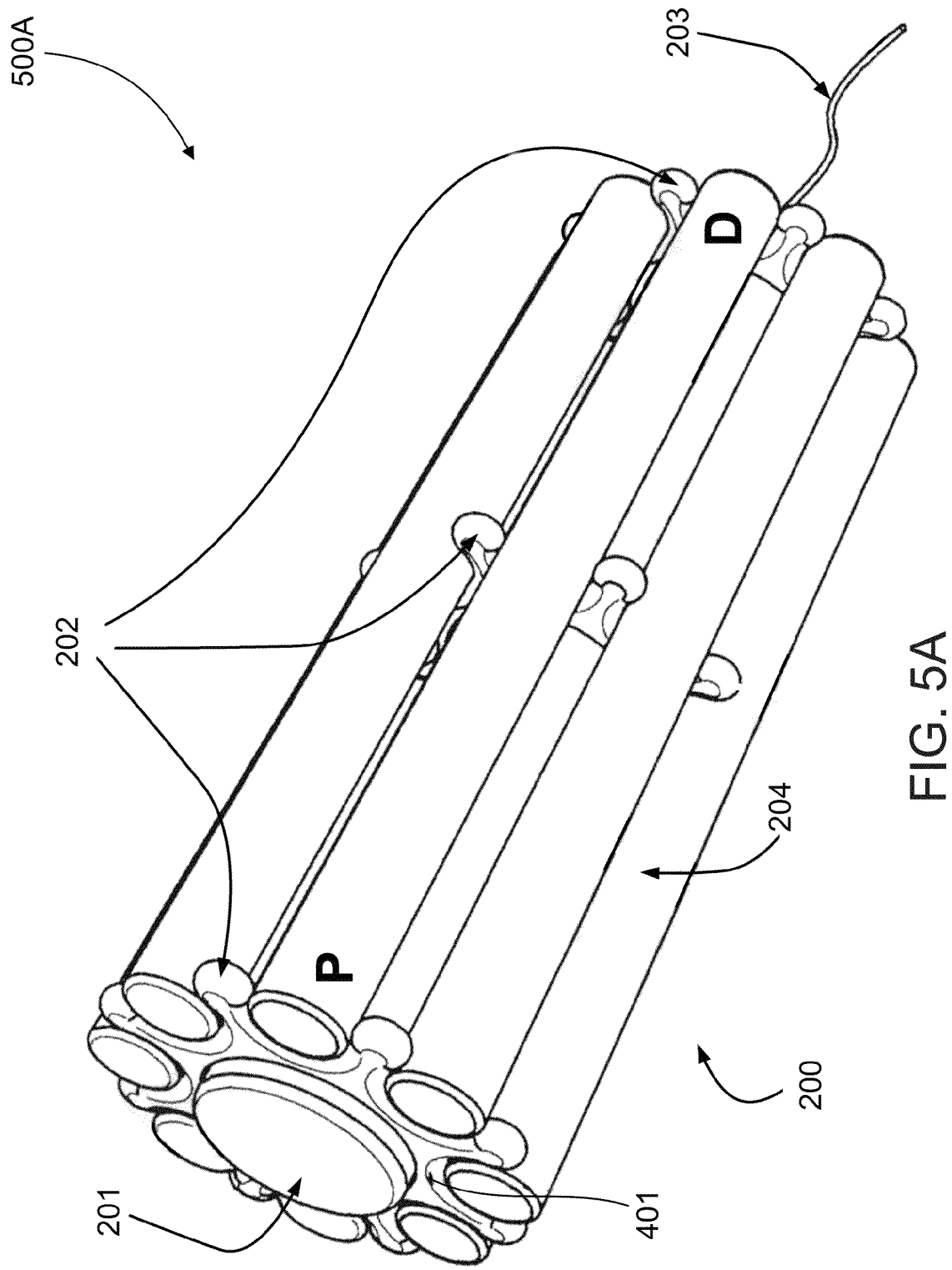
FIG. 5A is a schematic drawing depicting an exemplary supporting structure, exemplary coupling elements, and exemplary substance dispensers according to some embodiments of the present invention.

Reference is now also made to FIG. 5A, which is a schematic drawing depicting an exemplary supporting structure 201, exemplary coupling elements 202, and exemplary substance dispensers 204 according to some embodiments of the present invention. A supporting structure 201 may be coupled to a plurality of substance dispensers 204 by means of coupling elements 202 to which substance dispensers 204 snap into place. Optionally, substance dispensers 204 are cylindrical in form, longitudinally coupled to supporting structure 201 substantially along the full length of supporting structure 201. The number of substance dispensers 204 attached to supporting structure 201 may be configured according to therapeutic and/or diagnostic requirements. Substance dispensers 204 may be attached by a slight push into recesses of coupling elements 202 in a radiator fashion. The number of substance dispensers 204, for example, between 2 and 8, is determined by therapeutic needs; hence their distribution around the supporting structure 201 may vary. The width of the recesses may be adapted to the cut section of substance dispensers 204, according to needs and load of drug. In some embodiments, all of the surrounding substance dispensers 204 may have one type of substance so that only one substance is applied to the vaginal mucosa. In other embodiments, there may be a combination of substances, for example two substances, so that substance dispensers 204 containing a first substance are interleaved with substance dispensers 204 containing a second substance around supporting structure 201. For example, if A and B are drugs, and a delivery device 200 comprises coupling elements 202 with eight recesses, the distribution of drugs A and B may be A B A B A B A B, A A B B A A B B, A A A A B B B B, or any other permutation. This type of distribution may allow the design of release patterns that enhance an equal absorption of a drug all around a vagina and/or preferred absorption of a drug on one particular side of the vagina. Such an embodiment is designed to be inserted in a 360 degree non-oriented fashion. However, when a requirement exists to enhance delivery of a drug toward one particular vaginal wall, delivery device 200 may comprise markings to show the user the correct direction of application and/or orientation.

Figure 5B:
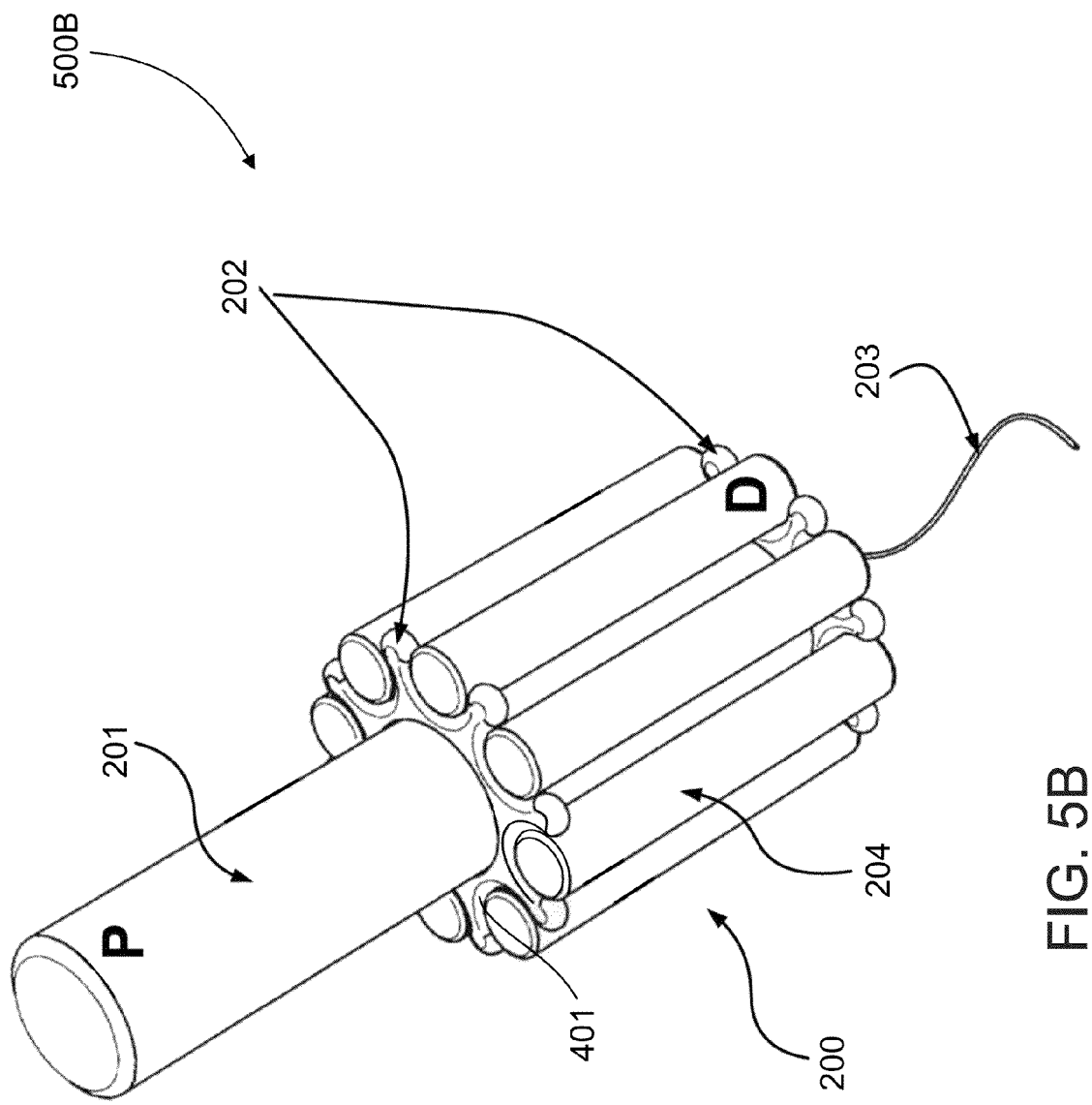
FIG. 5B is a schematic drawing depicting an exemplary delivery device comprising supporting structure, coupling elements, and substance dispensers according to some embodiments of the present invention.

Reference is now also made to FIG. 5B which is a schematic drawing depicting delivery device comprising a supporting structure, coupling elements, and substance dispensers according to some embodiments of the present invention.

FIG. 5B depicts substance dispensers 204, which are also depicted in FIG. 5A, however, in FIG. 5B shorter substance dispensers 204 are coupled at the distal (D) end of supporting structure 201. In this embodiment, delivery device 200 releases a substance across a smaller surface area on the vaginal walls than in the previous embodiment, and the release of the substance is directed toward the vaginal entrance.

Figure 5C:
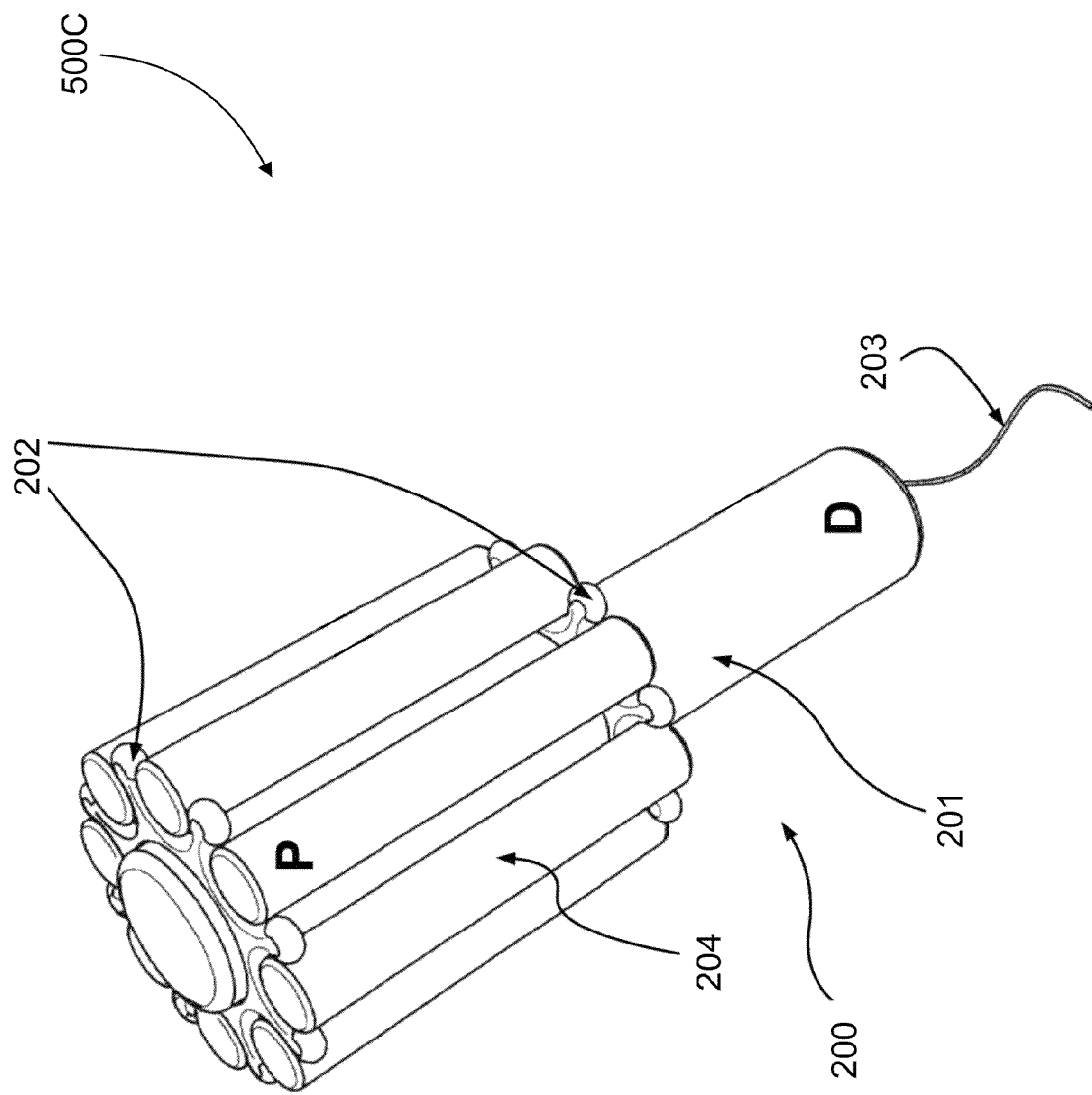
FIG. 5C is a schematic drawing depicting an exemplary delivery device comprising supporting structure, coupling elements, and substance dispensers according to some embodiments of the present invention.

Reference is now also made to FIG. 5C which depicts a configuration similar to the configuration of 5B, however, substance dispensers 204 are coupled to supporting structure 201 at the proximal (P) end rather than the distal (D) end to achieve another release pattern. Similarly, substance dispensers 204 may be configured for longitudinal placement along a central segment of supporting structure 201.

Figure 5D:
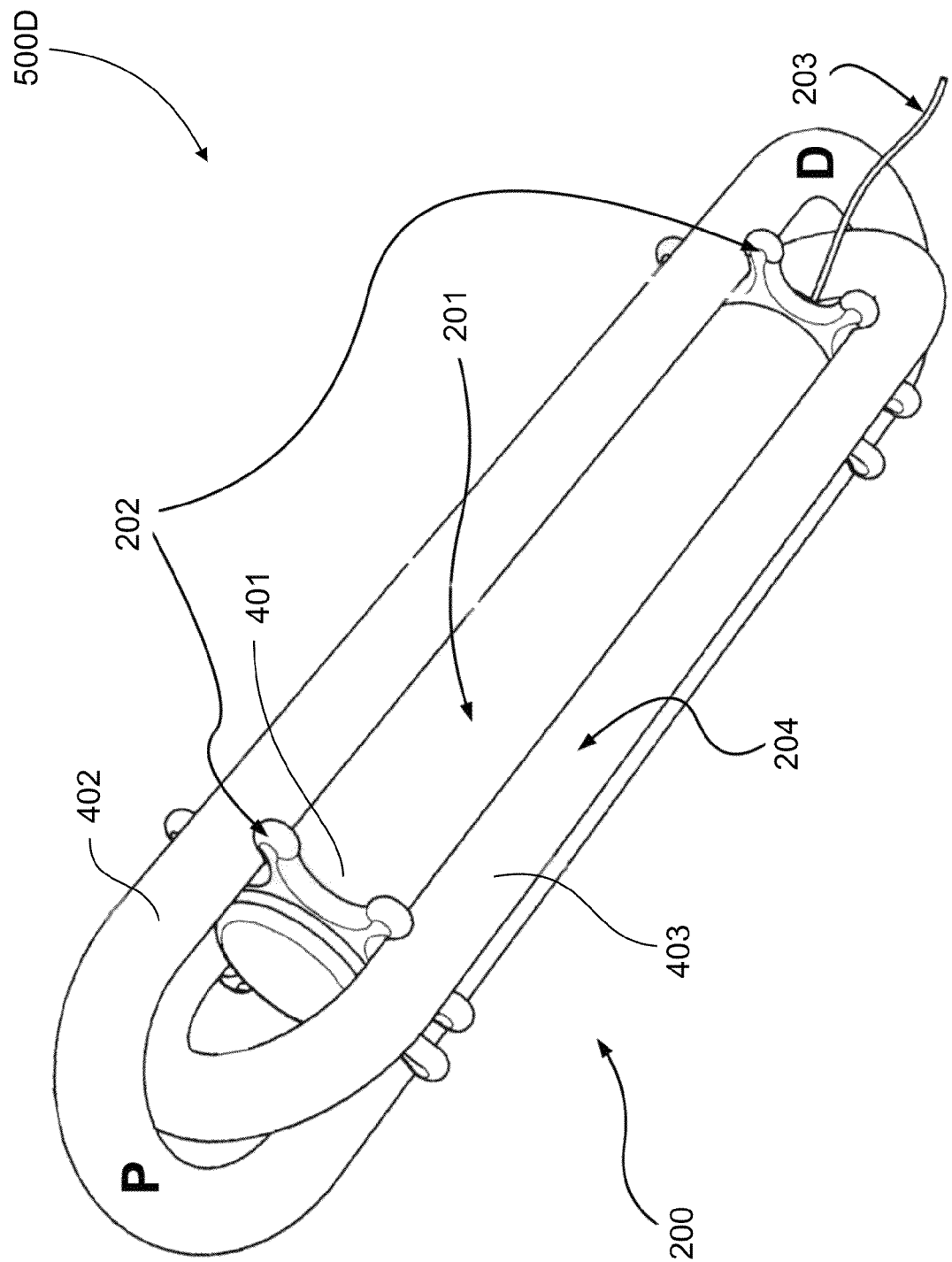
FIG. 5D is a schematic drawing depicting an exemplary delivery device comprising supporting structure, coupling elements, and substance dispensers according to some embodiments of the present invention.

Reference is now also made to FIG. 5D, which is a schematic drawing depicting an exemplary supporting structure 201, exemplary coupling elements 202, and exemplary substance dispensers 204 according to some embodiments of the present invention. Supporting structure 201 may be coupled to a plurality of substance dispensers 204 by means of coupling elements 202 to which substance dispensers 204 snap into place. Optionally, substance dispensers 402 and 403 are in the form of a torus, longitudinally coupled to supporting structure 201. In this embodiment, a drug is contained within flat ring substance dispensers 402 and 403 which are attached substantially along the full length of supporting structure 201, being inserted into the recesses 401 of coupling elements 202. Any number of such flat ring substance dispensers 402 and 403 may be used, and any number of recesses 401 may be available according to treatment requirements. In the described embodiment the angle between rings 402 & 403 is 90 degrees, but this may vary according to needs. Separate ring substance dispensers 402 & 403 may contain different drugs and/or different doses.

Figure 5E:
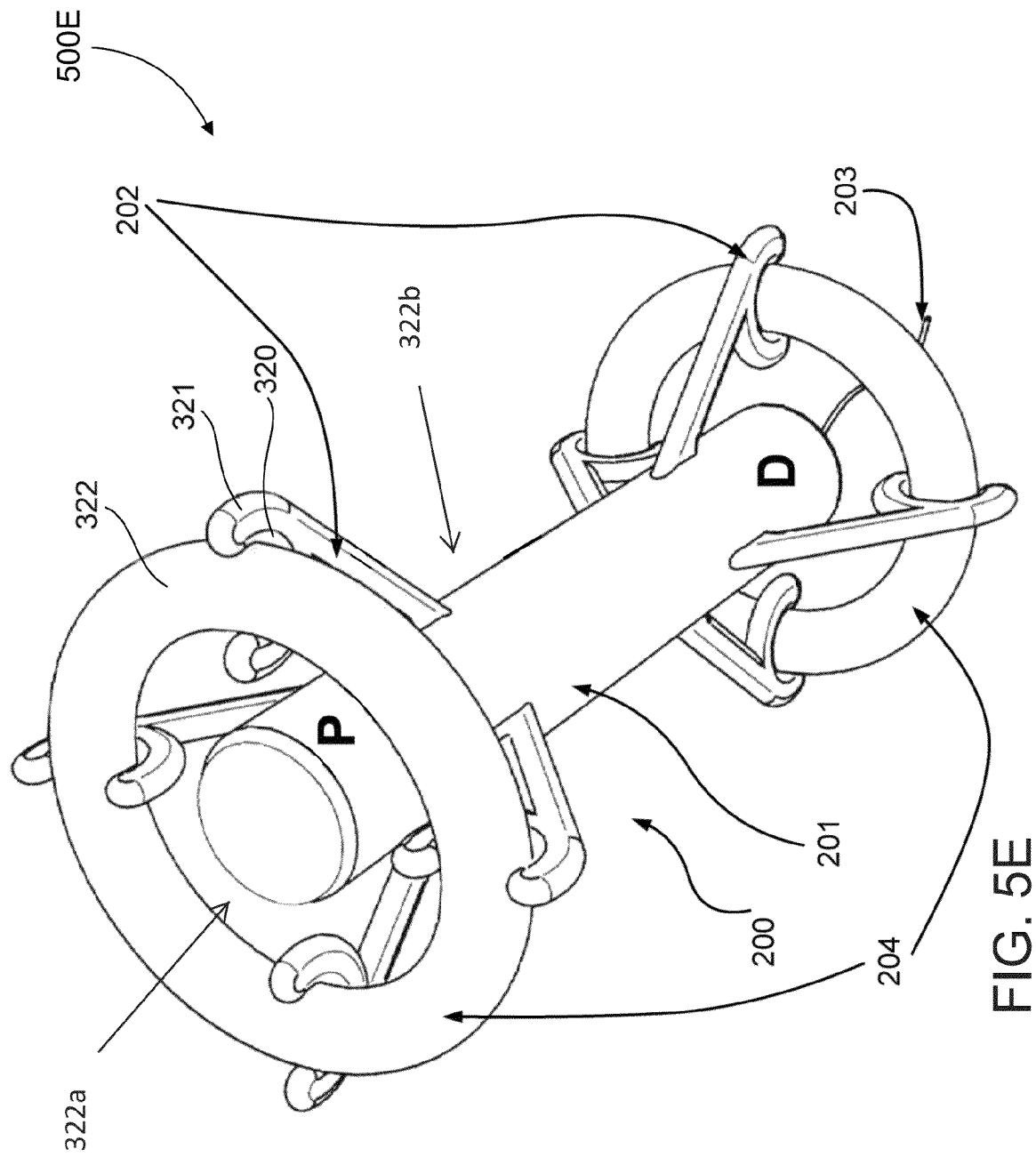
FIG. 5E is a schematic drawing depicting an exemplary delivery device comprising supporting structure, coupling elements, and substance dispensers according to some embodiments of the present invention.

Reference is now also made to FIG. 5E, which is a schematic drawing depicting an exemplary supporting structure 201, exemplary coupling elements 202, and exemplary substance dispensers 204 according to some embodiments of the present invention. This embodiment comprises supporting structure 201 and coupling elements 202 of FIG. 4B, wherein a plurality of substance dispensers 204 are coupled to supporting structure 201 by snapping them into the recesses 320 of coupling elements 202. Optionally, substance dispensers 204 are in the form of a torus, coupled to supporting structure 201 at the proximal (P) and/or distal (D) ends of supporting structure 201. The number of substance dispensers 204 attached to supporting structure 201 may be configured according to therapeutic and/or diagnostic requirements. Some exemplary embodiments of delivery devices 200 may comprise coupling elements 202 with arms which may extend at a plurality of angles, lengths, and directions, said arms each further comprising a coupling crescent 321 which has a recess 320. The arms may form a support for ring-shaped substance dispensers 322 that are inserted into recesses 320, perpendicular to a supporting structure 201. The radial spacing 322a between support structure 201 and dispensers 321 and the longitudinal spacing between dispensers 322 form a channel for passage of vaginal secretions. These arms and ring-shaped substance dispensers 322 may be located at both ends of supporting structure 201, but their locations and number may vary. The arms may be made of flexible materials to have sufficient flexibility to accommodate the vaginal mucosa and surrounding organs, and to be squeezed into an applicator. Optionally, one or more ring-shaped substance dispensers 322 may be coupled directly to supporting structure 201 in close proximity, and no coupling elements 202 are used.

Ring-shaped substance dispenser 322 may be attached to supporting structure 201, for example, by glue or by means of a groove across supporting structure 201 into which the narrow part of the ring may slide.

Figure 5G:
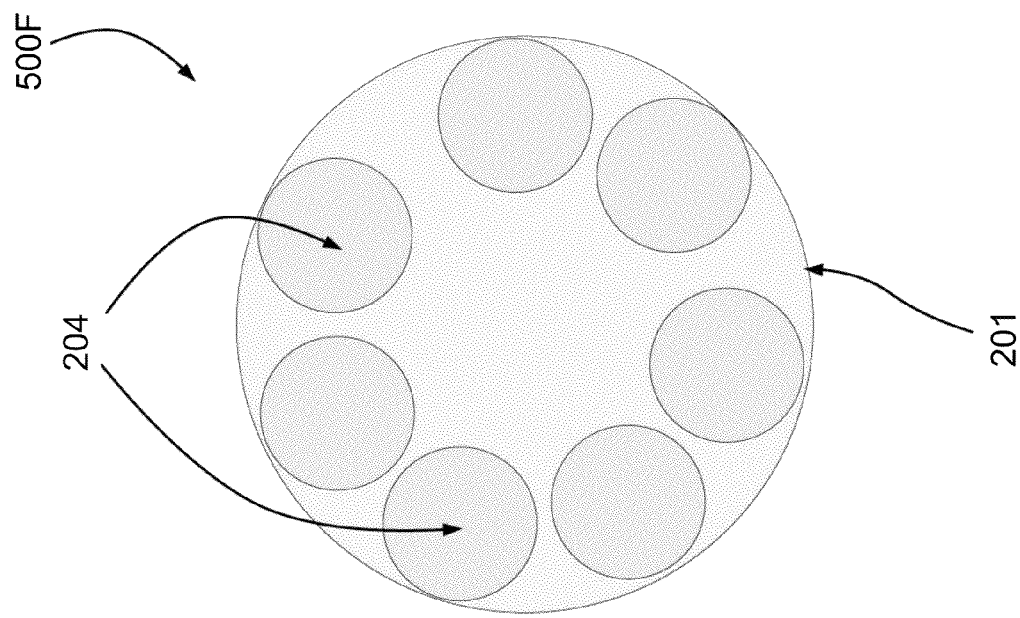
FIGS. 5F-5G are schematic drawings depicting an exemplary delivery device comprising supporting structure and substance dispensers according to some embodiments of the present invention.
Figure 5F:
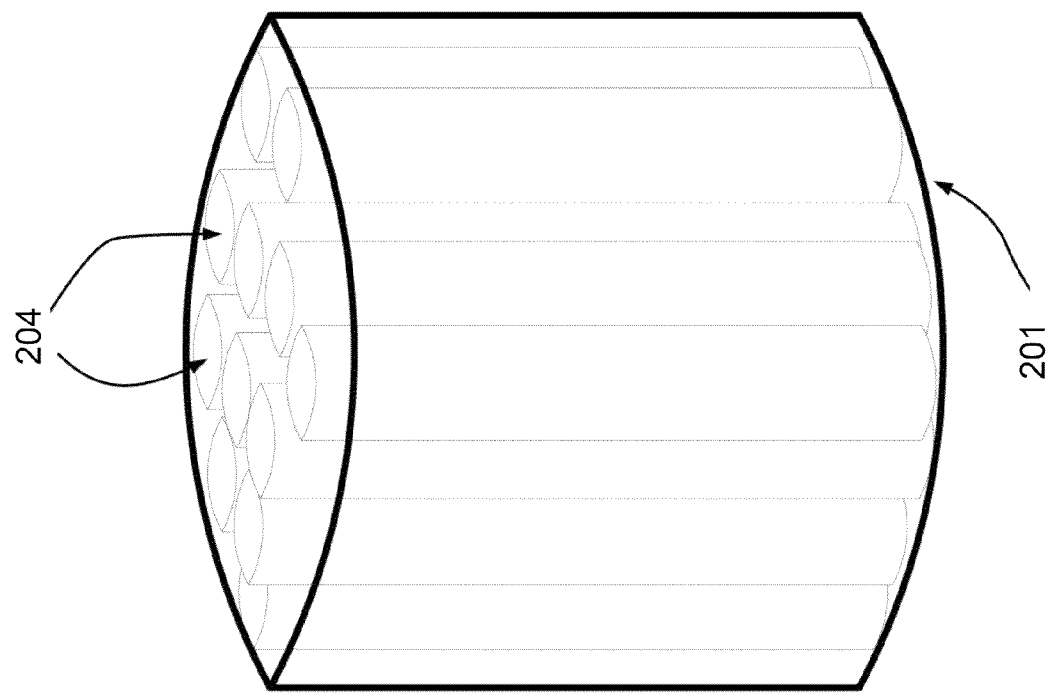

Reference is now also made to FIGS. 5F-5G, which are schematic drawings depicting an exemplary delivery device comprising supporting structure and substance dispensers according to some embodiments of the present invention. FIGS. 5F and 5G are side and top views, respectively. In this embodiment, supporting structure 201 contains substance dispensers 204 therein. Supporting structure 201 may be a bag, a packet, a receptacle, a set of surrounding belts, and/or a pouch. Size, shape, surface attributes, and pliability of supporting structure 201 and/or substance dispensers 204 are chosen according to requirements of treatment.

According to some embodiments of the current invention, a supporting structure 201 may be made of one or more materials, for example, elastomers such as thermo-plastic elastomers (TPE), silicones, nylon, and cardboard. Optionally, supporting structure 201 may be made of material that is degraded and/or absorbed by substances present in the vaginal lumen so that removal is not necessary.

According to some embodiments of the present invention, a substance dispenser may be in the shape of a cylinder, a torus, an ellipsoid, a sphere, a polyhedron, a crescent, a truncated cylinder, a truncated torus, a truncated ellipsoid, a truncated sphere, a truncated polyhedron, a truncated crescent, and/or an irregular solid. A substance dispenser may also be shaped as a truncated form of the aforementioned shapes or as an assembly of the aforementioned shapes and/or their truncated forms. Substance dispenser shapes, number of substance dispensers, method of attachment to a supporting structure 201, and/or location of attachment to supporting structure 201 may determine a release pattern of substance into a vaginal lumen.

Substance dispensers 204 may be made of any material known to control release of drugs, for example, silicone, ethylene vinyl acetate (EVA), and styrene butandiene block copolymer. Optionally, substance dispenser 204 may be made of material that is degraded and/or absorbed by substances present in the vaginal lumen so that removal is not necessary.

According to some embodiments of the present invention, a rate of release of a substance from a substance dispenser 204 may be determined by attributes of the surface of substance dispenser 204. The modular nature of a delivery device assembly, particularly of substance dispensers 204, provides a physician with flexibility to select a rate of release best suited to a desired course of therapy. For example, the surface of substance dispenser 204 may be smooth, coarse, perforated, striated, dimpled, particulate, permeable, and/or semi-permeable. Substance dispenser surface attributes, number of substance dispensers 204, method of attachment to a supporting structure 201, and/or location of attachment to supporting structure 201 may determine a substance rate of release into a vaginal lumen.

The design of the delivery device 200 allows it to be held in the vaginal lumen and to comprise as many substance dispensers 204 as may be needed. Several drugs may be released at the same time. Additionally or alternatively, delivery device 200 may simultaneously release drug absorption enhancers, for example, lactic acid which modifies pH in the vaginal lumen. Substance release may be directed to any chosen vaginal wall or pelvic target organ. Some embodiments allow delivery device 200 to be inserted in a 360 degree fashion with no need for specific orientation, while in others there may be a need to direct the insertion so that one facet of delivery device 200 is in direct contact with a specific organ and/or in close vicinity to blood vessels leading to a specific organ. Different configurations of delivery device 200 may be chosen (for example, size, shape, location, choice of substance, dosages, timing, and number of substance dispensers) to optimize delivery of one or more substances to one or more organs, according to exemplary embodiments of the present invention. Delivery device 200 may be configured to optimize the effect of a first substance and/or group of substances on a first organ, and to optimize the effect of a second substance and/or group of substances on a second organ. According to some embodiments of the present invention, delivery device 200 may be oriented at a plurality of coronal, transverse, and sagittal angles.

Figure 6:
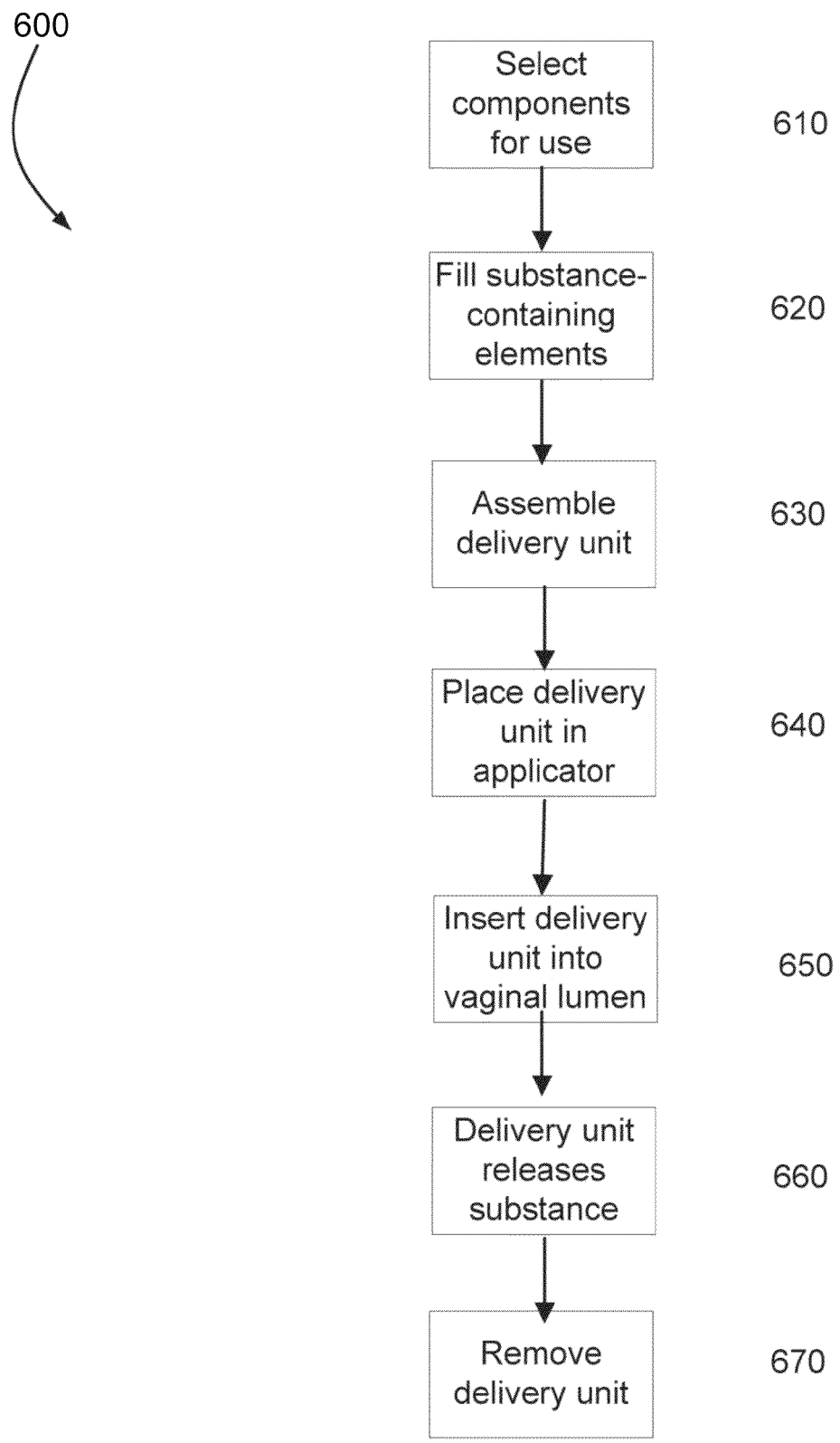
FIG. 6 is a flowchart depicting a method for using a delivery device for treatment, according to some embodiments of the present invention.

Reference is now also made to FIG. 6, which is a flowchart describing how a delivery device 200 may be assembled and used for treatment, according to an exemplary embodiment of the present invention. A user may assemble, insert, position, treat by means of, and remove delivery device 200 according to the requirements of treatment, according to an exemplary non-limiting embodiment of the present invention. The user selects modular component parts, such as a supporting structure 201, substance dispensers 204, coupling elements 202, substances and auxiliary components, such as an applicator, according to the requirements of a treatment plan 610. Substances to be released, such as drugs, are loaded into substance bearing components, for example, substance dispensers 204 and reservoirs in a supporting structure 620. The user assembles delivery device 200 from the component parts according a configuration designed to achieve a desired release pattern 630. Optionally, the user places delivery device 200 into an applicator which may facilitate properly placing delivery device 200 in a vaginal lumen 640. The user places delivery device 200 into the vaginal lumen in a position and/or orientation determined by the release pattern selected for treatment 650. When properly positioned, delivery device 200 delivers the substances to be released into the vaginal lumen according to the selected release pattern 660. The user removes delivery device 200 from the vagina when delivery device 200 has completed delivery of the substances to be released according to the selected release pattern 670. Optionally, the user removes delivery device 200 from the vagina by using a removal device.

Referring again to FIG. 2B, the illustration depicts a configuration allowing for large contact area of one or more drugs with large surface area of the vaginal lumen. Placement and dosages may be adjusted. Arrows A represent the local discharge into the vaginal fluid and onto the vaginal mucosa. Arrows B represent the ability to discharge the drug adjacent to a target organ, for example, the bladder, to facilitate supply of a drug to it. Arrow C represents the ability of a drug to be absorbed through the mucosa and to react on the mucosa as if it has been supplied systemically, for example, by ingestion. Arrow D represents the drug being absorbed from the delivery device 200 into the blood stream, acting on a specific organ, for example, the uterus. Arrow E represents systematic absorption into the blood stream and into distant organs. Referring again to FIG. 2C, the illustration depicts a configuration allowing for specific contact area of a drug with proximity to specific organs. Placing and dosages may be adjusted. For example, all substance dispensers 204 comprised by delivery device 200 may have an identical drug with identical doses. Alternatively, some substance dispensers 204 comprised by delivery device 200 may release non-identical doses of the same drug. Alternatively, separate substance dispensers 204 comprised by delivery device 200 may release different drugs from different dispensers simultaneously. The large arrows represent the flow of drug aimed at specific organs, while narrow arrows represent superficial flow of drug into vaginal fluid. In this embodiment, the number of substance dispensers 204 may be easily adjusted. The mechanism of action and distribution is similar to the one described for FIG. 2B. Use of configurable delivery device 200 allows for a variety of release patterns, for example, at a single spot, all along a vaginal lumen, any combination of spots and areas within a vaginal lumen, delivery directed to a vaginal apex, delivery aimed at an adjacent pelvic organ, and delivery aimed at a specific dense blood plexus.

Many drugs and/or drug combinations may be delivered by delivery device 200. For example, local reactants for treating various vaginal infections, anti-fungal drugs, and/or antibiotics may be delivered by delivery device 200. Examples of drugs which may be delivered by delivery device 200 include non-steroidal anti-inflammatory drugs to reduce uterine contractions and/or dysmenorrhea, muscle relaxants or beta-stimulants to improve blood flow, anticholinergic drug to reduce bladder contractions, and/or alpha stimulant to increase urethral resistance. Additionally or alternatively, reactants such as vaccinations, anti-HIV drugs, anti-chlamidial medications, and drugs which may not be used by people with impaired liver function may be delivered by delivery device 200. The vaginal route may serve as a reservoir for drugs needed on a long standing basis so that oral ingestion is minimized. Some reactants may have both local and systemic effect. For example, Metronidazole may be released on the vaginal walls, but also absorbed with systemic effect. Another example of a local and systemic reactant may be anti-viral treatment for Herpes infections. The aforementioned examples describe a short list, and many other drugs may be delivered alone or in combination with other drugs by delivery device 200. The length of time that delivery device 200 is present in a vaginal lumen may vary from several hours to several weeks, for example, 4 hours, 12 hours, 24 hours, 2 days, 1 week, 2 weeks, 1 month, and 2 months.

Figure 7:
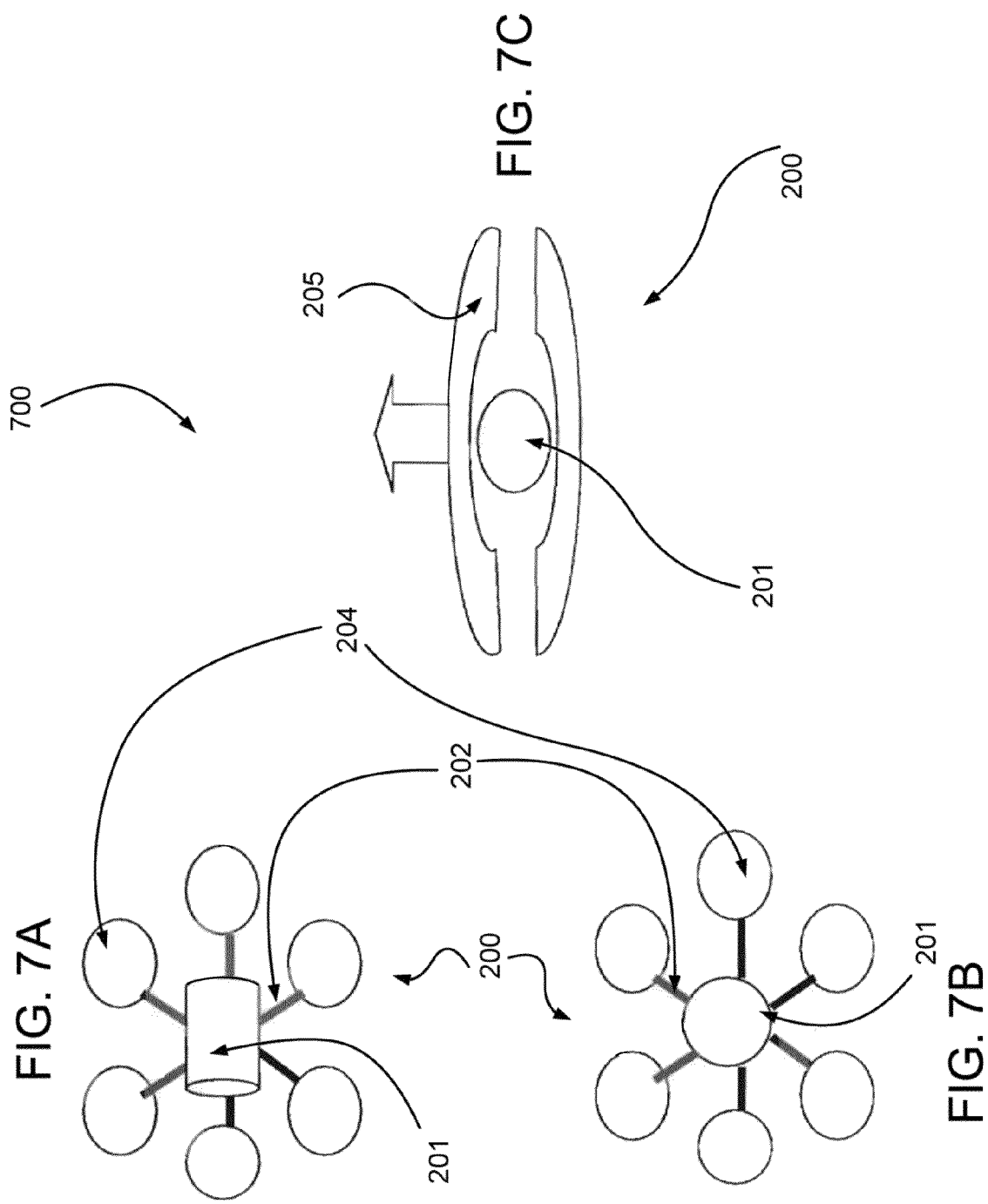
FIG. 7A is a schematic drawing depicting longitudinal section of a delivery device, according to some embodiments of the present invention.
FIG. 7B is a schematic drawing depicting cut section of a delivery device, according to some embodiments of the present invention.
FIG. 7C is a schematic drawing depicting cut section of a delivery device, according to some embodiments of the present invention.

Reference is now also made to FIGS. 7A-7B, which are a schematic drawings depicting longitudinal and cut sections, respectively, of a delivery device 200, according to some embodiments of the present invention. This embodiment is designed to be smaller than previously described embodiments and to be inserted into the vagina in a non-oriented fashion (360 degrees), providing yet another pattern of therapeutic substance delivery. It has a short supporting structure 201 and is coupled to many substance dispensers 204 by coupling elements 202, giving delivery device 200 a generally round or spiked appearance. This short delivery device 200 may be made of the same substances previously described, or substances that quickly degrade in the presence of vaginal substances, so that delivery device 200 degrades and/or is absorbed within the vagina with no need for its removal. Reference is now also made to FIG. 7C, which is a schematic drawing depicting a cut section of delivery device 200, according to some embodiments of the present invention. In this embodiment, delivery device 200 is configured to release a substance toward a specific vaginal wall, for example, an anterior wall, thus requiring delivery device 200 to be flattened to prevent it from rolling around. This may be achieved, for example, by configuring side wings 205. FIG. 7C shows a cut section of such a delivery device 200 with the arrow pointing towards the release site.

Figure 8:
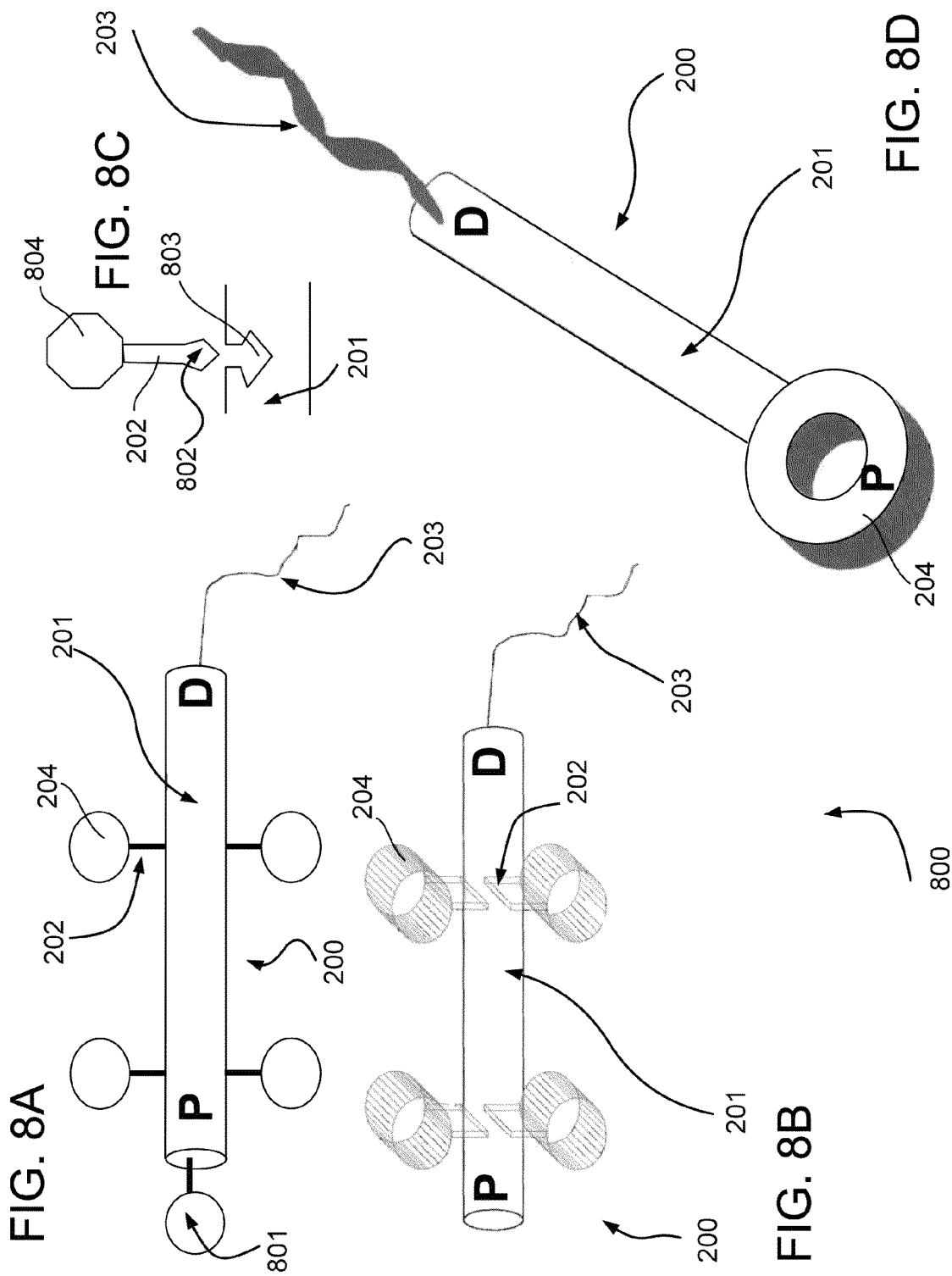
FIGS. 8A-8D are schematic drawings depicting an exemplary supporting structure, exemplary coupling elements, and exemplary substance dispensers according to some embodiments of the present invention.

Reference is now also made to FIGS. 8A-8D which are schematic drawings depicting an exemplary supporting structure 201, exemplary coupling elements 202, and exemplary substance dispensers 204 according to some embodiments of the present invention. These embodiments enable additional substance release patterns and depict another method of coupling. According to an embodiment of the invention, supporting structures 201 are connected to substance dispensers 204 by coupling elements 202. Substance dispensers 204 may be of various shapes and sizes, for example, balls, tubes, polygons, and various dimensions, for example, 5 to 15 millimeters each. Substance dispensers 204 may be distributed along the supporting structure 201 in any needed configuration, for example, as shown in FIG. 8A and FIG. 8B, or in one or more circles around the supporting structure 201 at the proximal end 801. Exemplary coupling elements 202 as illustrated in FIGS. 8A-8B comprise stalks. Attachment of substance dispensers 204 may be done by one of several mechanisms, for example, that shown in FIG. 8C, where coupling element 202 is pushed as a tucker 802 into a recess 803 within the walls of supporting structure 201 in a way that may prevent detachment. In another embodiment of the present invention, coupling element 202 is screwed into a small drilled hole within the wall of the supporting structure (not shown). In another embodiment of the present invention, as illustrated in FIG. 8D, a substance dispenser 204 is attached at the proximal end of a supporting structure 201, acting primarily at the top of a vagina. Such a substance dispenser 204 may also represent a plurality of substance dispensers 204 concentrated at the proximal end of supporting structure 201.

According to some embodiments of the present invention, a delivery device 200 may comprise a supporting structure 201 that releases a substance directly into a vaginal lumen. This configuration may be especially useful for very narrow vaginas. Optionally, supporting structure 201 may serve as an entire delivery device 200, i.e., without additional substance dispensers, and a substance to be released may be embedded within supporting structure 201 surface, for example, a polymer surface. Additionally or alternatively, one or more substance dispensers 204 may be coupled to supporting structure 201.

According to some embodiments of the present invention, a supporting structure 201 may comprise one or more reservoirs of one or more substances. A substance stored in a reservoir comprised by supporting structure 201 may be supplied to one or more substance dispensers 204 via a coupling element 202, and the substance may be subsequently released by one or more substance dispensers 204.

Reference is now also made to FIG. 9, which is a schematic illustration depicting adjustable (expandable) delivery devices 200 between lateral vaginal walls, according to some embodiments of the present invention. The embodiments described here are configured to be placed in a vaginal lumen and may simultaneously allow coitus. This is achieved by placing substance dispensers 204 against the vaginal walls and not obstructing the center of the vaginal lumen. A spring device 901 between lateral vaginal walls may comprise spherical type substance dispensers 204. A spring device 902 comprising rod-like dispensers 204 may adjust itself to vaginal width after release from an applicator, for example, by means of a spring 921. A spring device 903 with three rod-like substance dispensers may adjust itself, for example, by means of spring 921, to vaginal width after being released from an applicator such that two substance dispensers are adjacent to lateral vaginal walls, and a third substance dispenser is adjacent to a posterior or anterior vaginal wall. Additionally or alternatively, expansion of delivery device 901, 902, 903 may be achieved by other mechanisms (not shown), for example, release of a constraining force on a polymer element, balloon inflation, and expansion of an element that absorbs fluids from the vaginal lumen. An expandable delivery device self-adjusts its dimensions to conform to the spatial constraints of the vaginal lumen in which it is placed; this is in contrast to a non-expandable delivery device whose dimensions are fixed prior to placement in the vaginal lumen.

Figure 10:
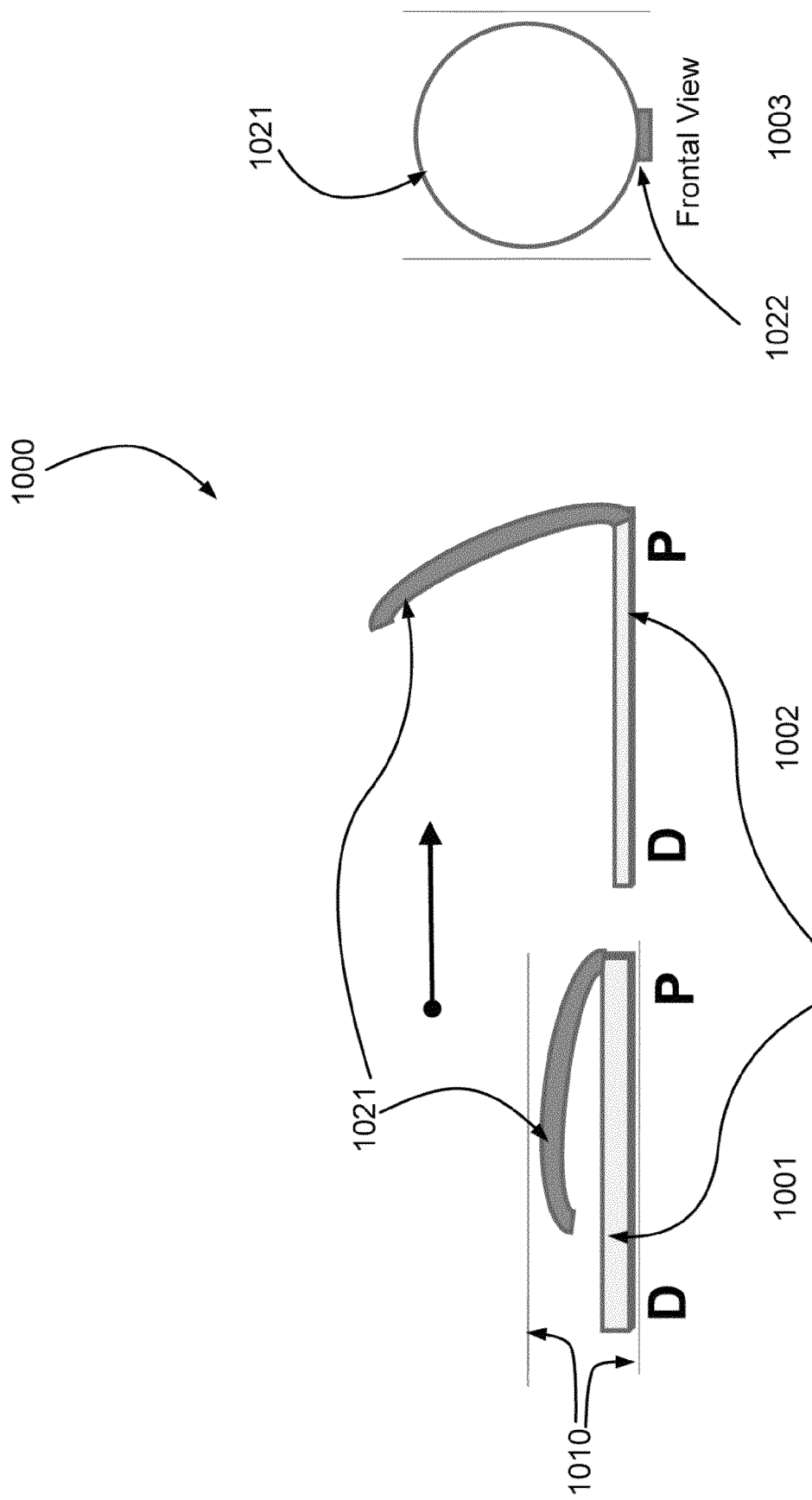
FIG. 10 is a schematic illustration depicting a delivery device configured to allow coitus, according to some embodiments of the present invention.

Reference is now also made to FIG. 10, which is a schematic illustration depicting a delivery device 1000 configured to allow coitus, according to some embodiments of the present invention. In such an embodiment, one or more substance dispensers are situated next to the periphery of the vaginal lumen without obstructing the center of the lumen to allow sexual penetration. A delivery device 1001 may be inserted into a vaginal lumen within an applicator 1010, wherein delivery device 1001 is a constricted and/or closed configuration. Upon removal from the applicator, delivery device 1002 may open and/or expand, for example, so that a substance dispenser is adjacent to a vaginal wall, and a supporting structure is adjacent to the cervix, or vice versa. Such a configuration may employ, for example, a hinged connection between supporting structure and substance dispenser, and a compressed spring may expand when released from an applicator. It should be noted that the supporting structure acts as a stabilizer to secure delivery device 1000 in place. In such a configuration, long bar 1022 may serve as a supporting structure and/or a substance dispenser. In other embodiments the ring 1021, which is attached to bar 1022 with a hinged connection, may serve as a supporting structure of the delivery device and/or a substance dispenser, according to need or design.

Optionally, device 1000 is inserted into a vaginal lumen manually, without an applicator.

Optionally or additionally, device 1000 is inserted into a vaginal lumen within a degradable tubular film, which disrupts when absorbing fluids and allows ring 1021 to be released into an open position.

According to some embodiments of the present invention, a substance dispenser 204 may comprise one or more reservoirs of one or more substances. A substance stored in a reservoir may be released through the surface of substance dispenser 204 that comprises the reservoir. The combination of substance dispenser 204 release rate and/or release rates over time and the quantity of substance stored in the reservoir may determine the period of time for which substance dispenser 204 releases substance. Optionally or alternatively, a first substance dispenser 204 comprising a reservoir of substance may be coupled to a second substance dispenser 204; substance from the reservoir comprised by the first substance dispenser 204 may be supplied to the second substance dispenser 204 via the coupling, and the substance may be subsequently released by the second substance dispenser 204.

According to some embodiments of the present invention, a delivery device 200 may comprise a sensor (not shown) configured to detect a concentration of a substance in a vaginal lumen. Examples of substances that may be detected include a metabolic substance, a pathogenic substance, a biological substance, and a medical substance. A controller may be configured to set a rate of release of one or more substances from substance dispensers 204 comprised by delivery device 200 based on the concentration detected by the sensor. For example, the sensor may detect glucose levels within vaginal fluid; the controller may cause the device to release more or less anti-glycemic agents on the basis of the detected glucose levels. Optionally, the rate of release may be a constant rate of release, a variable rate of release, an absence of release, and/or a combination of the preceding rates of release.

According to some embodiments of the present invention, a delivery device 200 may be inserted into the vagina by a no-self-touch technique. Some embodiments allow for insertion in a 360 degree fashion with no need for specific orientation, while in others there may be a need to direct the insertion so that one facet of delivery device 200 will be in direct contact with a specific organ and/or location of the vaginal lumen. Delivery device 200 may be inserted into the vaginal lumen by means of an applicator. The applicator may resemble an applicator used for insertion of a menstrual tampon. Optionally, an applicator may be used to maneuver delivery device 200 into an optimal position by adjusting the depth, lateral position, and/or orientation angles of delivery device 200 in the vaginal lumen. Additionally or alternatively, an applicator may be used to compress delivery device 200 that comprises an expanding element, for example, a spring, so that delivery device 200 does not expand until after it is placed into a vaginal lumen and the applicator is removed. Additionally or alternatively, the applicator may bear markings to assist in the placement of the applicator before releasing delivery device 200 contained within the applicator.

According to some embodiments of the present invention, a delivery device 200 may be removed by pulling a string 203 attached to the distal end of delivery device 200 and extending out of the vagina. Additionally or alternatively, delivery device 200 may comprise a small ring located at the most distal part of delivery device 200, close to the vaginal entrance, to aid in delivery device 200 removal.

According to some embodiments of the present invention, a delivery device 200 may be pre-assembled by a manufacturer and be packaged ready for use. Optionally, delivery device 200 may be packaged as a kit for assembly by a physician, a pharmacist, another health professional, and/or a patient. Additionally or alternatively, substances released by a substance dispenser 204 may be packaged within delivery device 200 by a manufacturer and/or substances released by substance dispenser 204 may be loaded into delivery device 200 by a health professional and/or a patient prior to use.

According to some embodiments of the present invention, some embodiments described heretofore may be extremely miniaturized to the size of a capsule for oral ingestion. All components of a delivery device 200 may be made of and/or coated with materials from which tablets are made or coated, for example, lactose powder, dibasic calcium phosphate, sucrose, corn (maize) starch, microcrystalline cellulose and modified cellulose, for example, hydroxymethyl cellulose. This may create a platform for various drugs to be ingested together as a single capsule. For example, a supporting structure 201 may be of length up to 10 millimeters, with various drugs being kept on it (e.g., as multiple substance dispenser rings on a cylinder). This may serve for co-treatment in cases of illnesses where several drugs are needed together, for example, Warfarine and Digoxin, and for some cases in which pharmacists are able to assemble drug combinations for a specific user.

According to some embodiments of the present invention, a miniaturized delivery device may be used as a drug releasing implant, either for systemic use (for example, hormone replacement therapy with multiple hormones), or implanted within a target organ (for example, chemotherapy).

According to some embodiments of the present invention, a delivery device may be used to deliver substances rectally.

According to some embodiments of the present invention, a delivery device may be used in veterinary medicine to treat animals.

It is expected that during the life of a patent maturing from this application many relevant carriers for the controlled release of drugs will be developed and the scope of the term controlled release of drugs is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and the include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An elongate device for delivery of at least one medical substance in a vaginal lumen, comprising:
   a configurable releasing mechanism in the form of a rod or a closed loop having a generally circular cross-section, comprising at least one substance release dispenser, that contains at least one medical substance and having a plurality of delivery configurations to actualize a plurality of predefined release patterns of said at least one medical substance; and
   an elongate supporting structure that supports thereon the positioning of said configurable releasing mechanism in the vaginal lumen,
   wherein said elongate supporting structure comprises an elongate element and also includes a plurality of coupling elements in the form of elongate elements that extending radially away from said elongate supporting structure and adapted to engage said configurable releasing mechanism and act as spacing elements that radially space said elongate supporting structure from said configurable releasing mechanism,
   wherein said coupling elements each terminate with a snap-fit coupling which can snap connect to one of said configurable releasing mechanism,
   wherein each of said configurable release mechanisms is adapted to be held by at least two of said coupling elements,
   such that said assembled device is sized and shaped to wholly fit within a vaginal canal.

2. The device of claim 1, wherein said configurable releasing mechanism comprises a plurality of substance dispensers each configured according to a pattern selected from said plurality of predefined release patterns, said supporting structure and said at least one of a plurality of substance dispensers being detachably coupled to one another.

3. The device of claim 2, wherein said supporting structure includes a plurality of separate support locations and wherein said configurable releasing mechanism is modular and can be selectively attached at any of said plurality of different support locations.

4. The device of claim 2 wherein said at least one substance dispenser is coupled to at least one of a plurality of predefined sites on said supporting structure.

5. The device of claim 4, wherein said device delivers different medical substances via different parts of said device, corresponding to different parts of said vagina, such that different medical substances may flow to different body organs and wherein at least one of said substance dispensers is configured to be coupled at a site on said supporting structure to effect placement at an optimal anatomical location to affect an organ, and at least one other of said substance dispensers is configured to be coupled at a site on said supporting structure at a different optimal anatomical location to affect a different organ.

6. The device of claim 5, wherein said at least one of said substance dispensers and said at least one other of said substance dispensers deliver substances simultaneously.

7. The device of claim 4, wherein said releasing mechanism self-adjusts its dimensions to conform to the spatial constraints of the vaginal lumen.

8. The device of claim 4, wherein said coupling enables situating said supporting structure and said at least one substance dispenser adjacent to the periphery of the vaginal lumen without occupying the center of the vaginal lumen to enable unhindered coitus.

9. The device of claim 2, wherein said supporting structure is configured for releasing a substance.

10. The device of claim 2, wherein said supporting structure comprises a reservoir of the at least one substance and is configured for dispensing the at least one substance via said substance dispensers.

11. The device of claim 2, wherein a first group of said plurality of substance dispensers releases a first group of substances and a second group of said plurality of substance dispensers releases a second group of substances.

12. The device of claim 2, wherein said at least one substance dispenser has a form that is at least one of a shape and an assembly of shapes;
   wherein said shapes are selected from a group consisting of a cylinder, a torus, an ellipsoid, a sphere, a polyhedron, a crescent, a truncated cylinder, a truncated torus, a truncated ellipsoid, a truncated sphere, a truncated polyhedron, a truncated crescent, and an irregular solid.

13. The device of claim 12, wherein the surface of said form is selected from a group consisting of smooth, coarse, perforated, striated, dimpled, particulate, permeable, and semi-permeable.

14. The device of claim 2, wherein at least one of said at least one substance dispenser and said supporting structure is at least one of absorbable and degradable by substances present within said vaginal lumen.

15. A device according to claim 14, wherein said at least one substance dispenser is at least one of absorbable and degradable by substances present within said vaginal lumen configured to remain in a vagina for at least 24 hours.

16. The device of claim 1, wherein said at least one substance dispenser is attached to said supporting structure by a means selected from the group consisting of including a fastener, a screw, a snap, a glue, a tucker, and a resin.

17. The device of claim 16, wherein said at least one substance dispenser is attached to said supporting structure by a snap connection.

18. The device of claim 1, wherein the at least one medical substance is selected from the group consisting of a drug, a chemical, a therapeutic material, a diagnostic material, a nutrient, a metabolic substance, a scent-emitting agent.

19. The device of claim 1, further comprising a sensor configured for detecting a concentration of a substance selected from the group consisting of a metabolic substance, a pathogenic substance, a biological substance, a chemical substance, and said at least one medical substance.

20. The device of claim 19, wherein said device comprises a controller configured to control a rate of release of the at least one medical substance according to said detecting.

21. The device of claim 20, wherein said wherein said rate of release is selected from the group consisting of an absence of release, a constant rate of release, and a variable rate of release.

22. A kit comprising the device of claim 1 and including at least one of the following items:
   i) a container for containing at least one medical substance;
   ii) a substance dispenser;
   iii) a supporting structure;
   iv) a medical substance;
   v) a member of a group consisting of a fastener, a screw, a snap, a glue, a resin, and a tucker;
   vi) a sensor for detecting a concentration of a substance;
   vii) a controller configured to control a rate of release;
   viii) an applicator; and
   ix) a removal device.

23. A device according to claim 1, wherein said organs comprise a bladder.

24. A device according to claim 1, wherein said different parts comprise different vaginal walls.

25. A device according to claim 24, wherein said different walls comprises anterior and posterior walls of the vagina.

26. A device according to claim 1, configured to remain in a vagina for at least 24 hours.

27. The device of claim 1, wherein said plurality of coupling elements each comprises at least one recess for insertion of a configurable releasing mechanism therein.

28. The device of claim 1, wherein each of said plurality of coupling elements includes at least 4 recesses.

29. The device of claim 1, wherein said plurality of coupling elements is between 2 and 4 coupling elements.

30. The device of claim 1, wherein said configurable releasing mechanism is cylindrical and is attached between two coupling elements and along at least a portion of said elongate element.

31. The device of claim 1, wherein said configurable releasing mechanism is a torus and is attached at an axial position of said elongate element.

32. The device of claim 1, wherein said configurable releasing mechanism extends past both ends of said elongate element.

33. The device of claim 1, comprising a plurality of configurable releasing mechanisms which substantially surround said elongate element.

34. The device of claim 1, wherein said coupling elements are flexible.

35. The device of claim 1, wherein said medical substance is a fluid.

36. The device of claim 1, wherein said medical substance is absorbed by vaginal fluid or mucous membrane.

37. The device of claim 1, wherein said coupling elements are arranged in a plurality of spaced apart groups, at least one first group near one end of said elongate support element.

38. The device of claim 1, loaded in a vaginal applicator.

39. The device of claim 1, wherein each of said snap-fit couplings engages a corresponding configurable releasing mechanism when said mechanism is pushed into a recess in said coupling element.

40. The device of claim 1, wherein said device defines at least one channel for passage of vaginal secretions, while said device is in operation within a vaginal cavity, between said elongate structure and at least a portion of said configurable releasing mechanism, said plurality of coupling elements lying within said channel.

41. The device of claim 1, wherein said elongate supporting structure is formed of an elastomer, silicone or nylon.

* * * * *